(12) United States Patent
Soriano et al.

(10) Patent No.: US 11,484,673 B2
(45) Date of Patent: Nov. 1, 2022

(54) ELECTRICALLY OPERATED AEROSOL GENERATION SYSTEM

(71) Applicant: JT International S.A., Geneva (CH)

(72) Inventors: Ivan Soriano, Amsterdam (NL); Steve Anavi, Paris (FR); Alexandre Prot, Paris (FR)

(73) Assignee: JT International SA

( * ) Notice: Subject to any disclaimer, the term of this patent is extended or adjusted under 35 U.S.C. 154(b) by 689 days.

(21) Appl. No.: 16/470,071

(22) PCT Filed: Jan. 2, 2018

(86) PCT No.: PCT/EP2018/050069
§ 371 (c)(1),
(2) Date: Jun. 14, 2019

(87) PCT Pub. No.: WO2018/122410
PCT Pub. Date: Jul. 5, 2018

(65) Prior Publication Data
US 2020/0008474 A1 Jan. 9, 2020

(30) Foreign Application Priority Data
Dec. 30, 2016 (EP) ..................... 16207559

(51) Int. Cl.
*A61M 15/06* (2006.01)
*A61M 11/04* (2006.01)
(Continued)

(52) U.S. Cl.
CPC ............. *A61M 15/06* (2013.01); *A24F 40/50* (2020.01); *A61M 11/042* (2014.02); *A24F 40/10* (2020.01);
(Continued)

(58) Field of Classification Search
CPC ................ A61M 15/06; A61M 11/042; A61M 2016/0021; A61M 2205/3334;
(Continued)

(56) References Cited

U.S. PATENT DOCUMENTS 5,269,327 A    12/1993   Counts et al.
9,884,157 B2    2/2018   Weitzel et al.
(Continued)

FOREIGN PATENT DOCUMENTS

EA          201691654 A1    1/2017
EP           2110033 A1    10/2009
(Continued)

OTHER PUBLICATIONS

International Search Report including Written Opinion for Application No. PCT/EP2018/050065 dated Apr. 10, 2018, 14 pages.
(Continued)

*Primary Examiner* — Truc T Nguyen
(74) *Attorney, Agent, or Firm* — Lerner, David, Littenberg, Krumholz & Mentlik, LLP

(57) ABSTRACT

An aerosol generation system for generation of an aerosol from an aerosol-forming precursor includes an electrically operated heating system to heat the precursor to generate the aerosol, a flow path for transmission of flow, including the aerosol, to a user, the heating system arranged in fluid communication with the flow path, and electrical circuitry. The electrical circuitry is configured to determine a characteristic associated with a second order time derivative of a property of electrical energy through the heating system, and to determine a property related to the flow of the flow path based on the characteristic of the second order time derivative.

15 Claims, 9 Drawing Sheets

(51) Int. Cl.
  *A24F 40/50* (2020.01)
  *A61M 16/00* (2006.01)
  *A24F 40/10* (2020.01)
  *A24F 40/60* (2020.01)

(52) U.S. Cl.
  CPC ...... *A24F 40/60* (2020.01); *A61M 2016/0021* (2013.01); *A61M 2205/3334* (2013.01); *A61M 2205/3368* (2013.01); *A61M 2205/502* (2013.01)

(58) Field of Classification Search
  CPC .... A61M 2205/3368; A61M 2205/502; A61M 15/008; A61M 2016/0027; A61M 2016/003; A61M 2205/3553; A61M 2205/3569; A61M 2205/3584; A61M 2205/3592; A61M 2205/3653; A61M 2205/8206; A61M 2230/63; A24F 40/50; A24F 40/10; A24F 40/60; A24F 40/46
  See application file for complete search history.

(56) References Cited

U.S. PATENT DOCUMENTS

| | | | |
|---|---|---|---|
| 10,477,893 | B2 | 11/2019 | Lord |
| 10,945,463 | B2 | 3/2021 | Dickens et al. |
| 11,129,418 | B2 | 9/2021 | Lord |
| 11,147,315 | B2 * | 10/2021 | Alarcon ............ G05D 23/1927 |
| 2014/0270727 | A1 | 9/2014 | Ampolini et al. |
| 2015/0313283 | A1 | 11/2015 | Collett et al. |
| 2016/0271347 | A1 | 9/2016 | Raichman |
| 2016/0331026 | A1 * | 11/2016 | Cameron ................ A24F 40/50 |
| 2017/0019951 | A1 | 1/2017 | Louveau et al. |
| 2017/0049151 | A1 | 2/2017 | Xue et al. |
| 2017/0135412 | A1 | 5/2017 | Cameron |
| 2017/0251725 | A1 | 9/2017 | Buchberger et al. |
| 2018/0020729 | A1 * | 1/2018 | Alarcon ............ G05D 23/1927 392/404 |
| 2021/0329977 | A1 * | 10/2021 | Sur ......................... H02J 50/20 |
| 2021/0345681 | A1 | 11/2021 | Cameron |

FOREIGN PATENT DOCUMENTS

| | | |
|---|---|---|
| EP | 2468116 A1 | 6/2012 |
| EP | 2797448 A2 | 11/2014 |
| GB | 2537121 A | 10/2016 |
| WO | 2013060781 A1 | 5/2013 |
| WO | 2013098397 A2 | 7/2013 |
| WO | 2013098398 A2 | 7/2013 |
| WO | 2015124878 A1 | 8/2015 |
| WO | 2016030661 A1 | 3/2016 |

OTHER PUBLICATIONS

International Search Report including Written Opinion for Application No. PCT/EP2018/050069 dated Mar. 14, 2018, 17 pages.
International Search Report including Written Opinion for Application No. PCT/EP2018/050070 dated Apr. 19, 2018, 15 pages.
International Search Report including Written Opinion for Application No. PCT/EP2018/050071 dated Mar. 14, 2018, 18 pages.
Soriano et al., U.S. Appl. No. 16/469,507, filed Jun. 13, 2019, titled "Electrically Operated Aerosol Generation System".
Soriano et al., U.S. Appl. No. 16/470,102, filed Jun. 14, 2019, titled "Electrically Operated Aerosol Generation System".
Soriano et al., U.S. Appl. No. 16/470,875, filed Jun. 18, 2019, titled "Electrically Operated Aerosol Generation System".

* cited by examiner

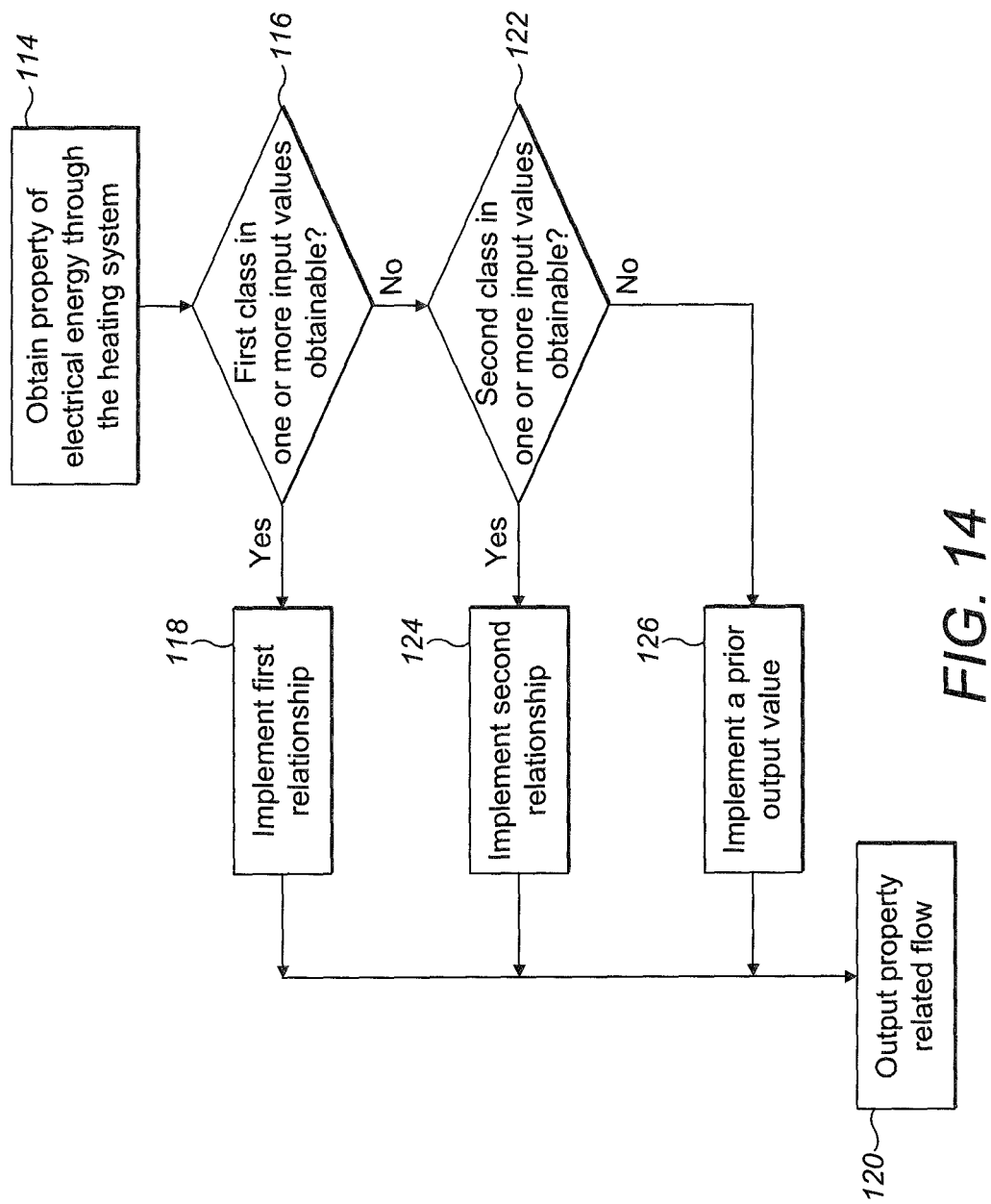

ELECTRICALLY OPERATED AEROSOL GENERATION SYSTEM

CROSS-REFERENCE TO RELATED APPLICATIONS

The present application is a national phase entry under 35 U.S.C. § 371 of International Application No. PCT/EP2018/050069, filed Jan. 2, 2018, published in English, which claims priority to European Patent Application No. 16207559.2 filed Dec. 30, 2016, the disclosures of which are incorporated herein by reference.

TECHNICAL FIELD

The present disclosure relates to the field of electrically operated aerosol generation systems in which an aerosol is formed from an aerosol-forming precursor and delivered to a user. In particular the disclosure relates to determining properties of flow through said systems, which includes the aerosol.

BACKGROUND

Aerosol generation systems comprise a storage portion for storing an aerosol-forming precursor. The precursor may comprise a liquid. A heating system may be formed of one or more electrically activated resistive heating elements, which are arranged to heat said precursor to generate the aerosol. The aerosol is released into a flow path extending between an inlet and outlet of the system. The outlet may be arranged as a mouthpiece, which a user inhales through for delivery of the aerosol to the user.

The system may implement measurement of the depletion of the precursor to determine the quantity of one or more components thereof delivered to a user. Measurement may also be implemented to determine the quantity of precursor that remains in the storage portion so that the user can be notified when replenishment is required. Such measurement may be implemented by means of a flow meter or a level sensing system associated with the storage portion. It may be desirable to develop a cost-effective and/or reliable means for measuring depletion.

In spite of the effort already invested in the development of aerosol generation systems further improvements are desirable.

SUMMARY

The present disclosure provides an aerosol generation system for generation of an aerosol from an aerosol-forming precursor, the system comprising: an electrically operated heating system to heat said precursor to generate the aerosol; a flow path for transmission of flow, including the aerosol, to a user; the heating system arranged in fluid communication with the flow path; electrical circuitry to determine a characteristic associated with a second order time derivative of a property of electrical energy through the heating system, and to determine a property related to the flow of the flow path based on the characteristic of the second order time derivative.

By implementing determination of the characteristic from the second order time derivative it has been found that the characteristic (such as an amplitude, period, rise time or time of peak or area associated with an oscillation in said property) may be most accurately located and determined. Consequently, the property of the flow may be most accurately calculated. In particular, in implementations wherein the property (e.g. power, current or voltage) is maintained as a constant or to maintain a constant temperature, it has been found that the second order time derivative converges faster to a nominal value than current without numerical differentiation, whereby the characteristic can be most easily determined.

In embodiments, the property related to the flow is one or more of: an amount of one or more components of the aerosol; a start of an inhale; an end of an inhale; a duration of an inhale. "amount" may refer to a numerical quantity (e.g. a mass) as opposed to the presence or absence of the one or more components.

In embodiments, the characteristic comprises one or more of: an amplitude; a period; an area bounded by the maxima and/or minima of the oscillation from which an intensity, i.e. flow rate, of the inhalation can be inferred.

In embodiments, a characteristic of said feature is directly related to an amount of the one or more components of aerosol dispensed. By directly related it is meant that the greater the magnitude of the feature the greater the amount of the component dispensed, e.g. via direct proportionality or other mathematical function relationship.

In embodiments, the circuitry may implement control to regulate a property of the heating system as a constant, e.g. a temperature of the heating system is regulated to a target temperature or a voltage over the heating system is regulated to a target voltage. Said control may be implemented by pulse width modulation (PWM) or other appropriate means such as a DC:DC converter. In embodiments, a temporal displacement of said regulated property from a target magnitude may be determined as a result of an inhalation through the flow path and cooling of the heating system. The characteristic associated with a property of electrical energy can be based at least partially on said displacement.

In embodiments, the circuitry may implement measurement of a temperature of the heating system, e.g. by measuring an electrical resistance of the heating system and determining a temperature from said resistance based on an empirical relationship between the resistance and temperature or by a dedicated temperature sensor.

The present disclosure provides a method of determining a property of a flow of an aerosol generation system, the method comprising: determining a characteristic associated with a second order time derivative of a property of electrical energy through a heating system; determining the property related to the flow based on the characteristic of the second order time derivative. The method may implement any method of embodiments disclosed herein.

The present disclosure provides an aerosol generation system for generation of an aerosol from an aerosol-forming precursor, the system comprising: an electrically operated heating system to heat said precursor to generate the aerosol; a flow path for transmission of flow, including the aerosol, to a user; the heating system arranged in fluid communication with the flow path; electrical circuitry to determine a feature of an oscillation of a property of electrical energy through the heating system, the oscillation due to initiation and/or termination of a user inhale through the flow path, and to determine an amount of one or more components of aerosol dispensed in the inhale based (including at least partially based) on the feature of the oscillation.

By at least partially basing calculation of the amount of one or more components of aerosol dispensed in the inhale on a characteristic of oscillation, which is due to initiation and/or termination of the user inhale, the characteristics during the entire inhalation may not be required to be determined, for example, if only one of said initiation or termination oscillations can be identified.

In embodiments, the feature comprises one or more of: an amplitude; a period; an area bounded by the maxima and/or minima of the oscillation from which an intensity, i.e. flow rate, of the inhalation can be inferred.

It is to be understood that the oscillation due to initiation and/or termination of a user inhale refers to the change or fluctuation in the property of the electrical energy at the respective start and end of an inhalation, and in particular not an overall oscillation that may occur from start to end of an inhalation. The duration of the oscillation due to initiation and/or termination of a user inhale may for example be less than 10 or 5% of the overall duration of the inhalation. In embodiments, this fluctuation may be particularly apparent from the second order time derivative.

In embodiments, a magnitude of said feature is directly related to an amount of the one or more components of aerosol dispensed. By directly related it is meant that the greater the magnitude of the feature the greater the amount of the component dispensed, e.g. via direct proportionality or other mathematical function relationship.

The present disclosure provides a method of determining a feature of an oscillation of a property of electrical energy through a heating system, the oscillation due to initiation and/or termination of a user inhale through the flow path, determining an amount of aerosol dispensed in the inhale based on the feature of the oscillation. The method may implement any method of embodiments disclosed herein.

The present disclosure provides an aerosol generation system for generation of an aerosol from an aerosol-forming precursor, the system comprising: an electrically operated heating system to heat said precursor to generate the aerosol; a flow path for transmission of flow, including the aerosol, to a user; the heating system arranged in fluid communication with the flow path. The circuitry to: measure a property of the electrical energy through the heating system; determine one or more characteristics from said measured property of the electrical energy (e.g. during a user inhalation through the flow path, which imparts a cooling effect on the heating system that can be determined by said measured property); select, based on the determined characteristics, one from a plurality of different empirical relationships between the measured property of the electrical energy and a property of the flow; implement said relationship to determine the property of the flow.

By selecting a particular empirically obtained relationship, which is to relate the characteristics of the electrical energy to the property of the flow, based on a property of the measured electrical energy, the most appropriate relationship of several can be implemented to most accurately calculate said property of the flow.

In embodiments the property of the electrical energy may comprise the electrical current or power through or the electrical potential over the heating system. All of which can be conveniently measured by the circuitry, e.g. by various current and/or electrical potential measuring implementations.

In embodiments the property related to the flow is an amount of one or more components of the aerosol in the flow path, wherein the aerosol is generated from the precursor by an atomizer of the system. The flow may also comprise air sucked through the flow path by a user inhalation.

In embodiments, the characteristic is based on one or more of an: amplitude or period or area of an oscillation of said electrical energy or a time derivative thereof; an initiation time of a user inhale through the flow path; a duration of a user inhale through the flow path; a duration of electrical energy applied to the heating system. By selecting the amplitude or period or area of an oscillation of said electrical energy, a determination of the intensity of the inhalation, e.g. the flow rate, may be provided.

In embodiments, the empirical relationship comprises an empirically obtained mathematical formula. The empirical relationship may comprise an output value as the property of the flow. The output value may be related to one or more input values, each comprising the determined characteristic or another characteristic of the flow (e.g. the same characteristics used to select the relationship may be used as input and/or different characteristics).

In embodiments the electrical circuitry is configured to determine if said first one or more input values can be obtained from the measured property of the electrical energy, and to select said relationship based on the input values obtained. By selecting the relationship based on whether the associated input values can all be obtained, only a relationship that can provide a representative output value may be implemented.

In embodiments, a first relationship comprises as input a first set of one or more input values and a second relationship comprises a different second set of one or more input values, the circuitry to implement the first relationship if the first set of input values are obtainable else to implement the second relationship if the second set of input values are obtainable. By selecting a second relationship for which the input values can all be obtained instead of a first relationship for which the one or more input values cannot be obtained, a representative output can be obtained.

In embodiments, the second set of input values form a subset of the first set of input values. By selecting the second set of input values to consist of one or more of the first set of input values (whilst being numerically fewer than the first set), the second set can be determined when partially determining the first set, hence the second set does not require separate steps of computation to obtain.

In embodiments, the first set of one or more input values includes amplitude or period or an area of an oscillation of said electrical energy or a time derivative thereof, and the second set of one or more input values does not include an amplitude of an oscillation or said electrical energy or a time derivative thereof. By selecting the first set to include amplitude or period or an area of an oscillation, the first relationship can be based on intensity of the inhalation, e.g. the flow rate, and provides an accurate output value, and by not basing the second relationship on intensity a less accurate, but more reliable second relationship is provided.

In embodiments, the first and second set of input values includes a duration of a user inhale through the flow path and/or a duration of electrical energy applied to the heating system (e.g. a duration of an actuation of a vaping button). By selecting common input values to include said durations, the duration of an inhalation through the flow path can be accounted for, as opposed to just the flow rate, when determining the overall quantity of aerosol delivered for an inhalation.

In embodiments, the circuitry is configured such that if a set of input values is unobtainable, the output value is determined from an output value determined from a prior user inhale. By determining the output value from a prior inhalation in the instance that the first (or both first and second) relationship cannot be implemented (e.g. due to the associated input values not being obtainable), the system includes a reliable means for determining an output value.

The present disclosure provides a method of determining a property of a flow of an aerosol generation system, the method comprising: measuring a property of the electrical energy through the heating system; determining one or more characteristics from said measured property of the electrical energy; selecting, based on the determined characteristics, one from a plurality of different empirical relationships between the measured property of the electrical energy and a property of the flow; implementing said relationship to determine the property of the flow. The method may implement any method of embodiments disclosed herein.

The present disclosure provides an aerosol generation system for generation of an aerosol from an aerosol-forming precursor, the system comprising: an electrically operated heating system to heat said precursor to generate the aerosol; a flow path for transmission of flow, including the aerosol, to a user; the heating system arranged in fluid communication with the flow path; electrical circuitry to apply a predetermined amount of electrical energy to the heating system to stabilise a property of electrical energy through the heating system, the electrical circuitry to determine a property related to the flow of the flow path based on the stabilised property of the electrical energy through the heating system, wherein the property related to the flow is one or more of: an amount of one or more components of the aerosol.

By applying a predetermined amount of electrical energy to the heating system to stabilise a property of the electrical energy therethrough, a particular feature of the property of the electrical energy (such as an amplitude, period or area of an oscillation) may be extracted with increased accuracy and thus used to determine the property related to the flow with corresponding increased accuracy.

The present disclosure provides a method of determining a property of a flow of an aerosol generation system, the method comprising: applying a predetermined amount of electrical energy to a heating system to stabilise a property of electrical energy through the heating system; determining the property related to the flow based on the stabilised property of the electrical energy through the heating system, wherein the property related to the flow is one or more of: an amount of one or more components of the aerosol.

The present disclosure provides a computer program or electrical circuitry or a computer readable medium including the computer program to implement one or more of the previously disclosed methods.

BRIEF DESCRIPTION OF THE FIGURES

Aspects, features and advantages of embodiments of the present disclosure will become apparent from the following description of embodiments in reference to the appended drawings, in which like numerals denote like elements.

FIG. 14 is a flow diagram showing embodiment processes implemented by the system of FIG. 1 to determine a property of flow through said system, wherein the property is determined using one of a plurality of different relationships.

DETAILED DESCRIPTION OF EMBODIMENTS

Figure 1:
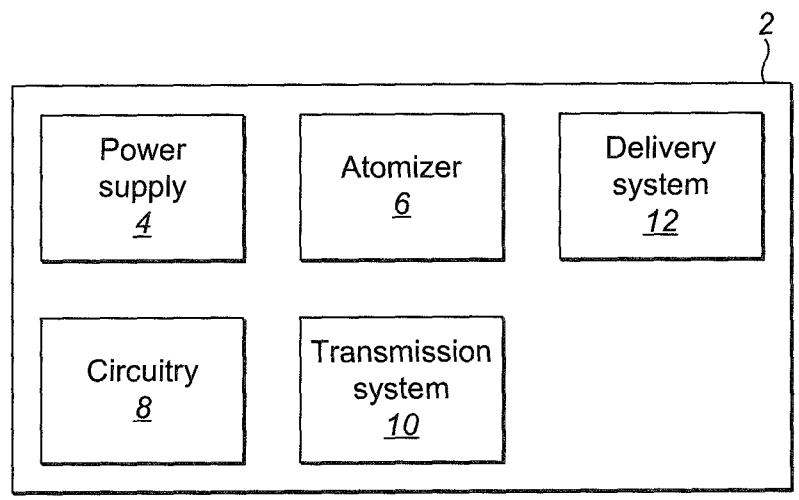
FIG. 1 is a block system diagram showing embodiment componentry of an aerosol generation system.

Before describing several embodiments of an aerosol generation system, it is to be understood that the system is not limited to the details of construction or process steps set forth in the following description. It will be apparent to those skilled in the art having the benefit of the present disclosure that the system is capable of other embodiments and of being practiced or being carried out in various ways.

The present disclosure may be better understood in view of the following explanations:

As used herein, the term "aerosol generation apparatus" or "apparatus" may include a smoking apparatus to deliver an aerosol to a user, including an aerosol for smoking, by means of an aerosol generating unit (e.g. a heater or atomiser which generates a vapour which condenses into an aerosol before delivery to an outlet of the apparatus at, for example, a mouthpiece, for inhalation by a user). An aerosol for smoking may refer to an aerosol with particle sizes of 0.5-7 microns. The particle size may be less than 10 or 7 microns. The apparatus may be portable. "Portable" may refer to the apparatus being for use when held by a user. The apparatus may be adapted to generate a variable amount of aerosol, e.g. by activating an atomizer for a variable amount of time (as opposed to a metered dose of aerosol), which can be controlled by a trigger. The trigger may be user activated, such as a vaping button and/or inhalation sensor. The apparatus may be adapted to generate a variable amount of aerosol, e.g. by activating an atomizer for a variable amount of time (as opposed to a metered dose of aerosol), which can be controlled by a trigger. The trigger may be user activated, such as a vaping button and/or inhalation sensor. The inhalation sensor may be sensitive to the strength of inhalation as well as the duration of inhalation so as to enable more or less vapour to be provided based on the strength of inhalation (so as to mimic the effect of smoking a conventional combustible smoking article such as a cigarette, cigar or pipe, etc.). The apparatus may include a temperature regulation control such as for example a Proportional, Integral, Differential (PID) controller to quickly drive the temperature of the heater and/or the heated aerosol generating substance (aerosol pre-cursor) to a specified target temperature and thereafter to maintain the temperature at the target temperature regardless of the amount of substrate (precursor) available at the aerosol generating unit and regardless of the strength with which a user inhales.

As used herein, the term "aerosol generation system" or "system" may include the apparatus and optionally other circuitry/componentry associated with the function of the apparatus, e.g. a peripheral device and/or other remote computing device.

As used herein, the term "aerosol" may include a suspension of precursor as one or more of: solid particles; liquid droplets; gas. Said suspension may be in a gas including air. Aerosol herein may generally refer to/include a vapour. Aerosol may include one or more components of the precursor.

As used herein, the term "aerosol-forming precursor" or "precursor" or "aerosol-forming substance" or "substance" may refer to one or more of a: liquid; solid; gel; other substance. The precursor may be processable by an atomizer of the apparatus to form an aerosol as defined herein. The precursor may comprise one or more of: nicotine; caffeine or other active component. The active component may be carried with a carrier, which may be a liquid. The carrier may include propylene glycol or glycerine. A flavouring may also be present. The flavouring may include Ethylvanillin (vanilla), menthol, Isoamyl acetate (banana oil) or similar.

As used herein, the term "electrical circuitry" or "electric circuitry" or "circuitry" or "control circuitry" may refer to, be part of, or include one or more of the following or other suitable hardware or software components: an Application Specific Integrated Circuit (ASIC); electronic/electrical circuit (e.g. passive components, which may include combinations of transistors, transformers, resistors, capacitors); a processor (shared, dedicated, or group); a memory (shared, dedicated, or group), that may execute one or more software or firmware programs; a combinational logic circuit. The electrical circuitry may be centralised on the apparatus or distributed, including distributed on board the apparatus and/or on one or more components in communication with the apparatus, e.g. as part of the system. The component may include one or more of a: network-based computer (e.g. a remote server); cloud-based computer; peripheral device. The circuitry may be implemented in, or functions associated with the circuitry may be implemented by, one or more software or firmware modules. The circuitry may include logic, at least partially operable in hardware.

As used herein, the term "processor" or "processing resource" may refer to one or more units for processing including an ASIC, microcontroller, FPGA, microprocessor, digital signal processor (DSP) capability, state machine or other suitable component. A processor may include a computer program, as machine readable instructions stored on a memory and/or programmable logic. The processor may have various arrangements corresponding to those discussed for the circuitry, e.g. on-board and/or off board the apparatus as part of the system.

As used herein, the term "computer readable medium/media" may include conventional non-transient memory, for example one or more of: random access memory (RAM); a CD-ROM; a hard drive; a solid state drive; a flash drive; a memory card; a DVD-ROM; a floppy disk; an optical drive. The memory may have various arrangements corresponding to those discussed for the circuitry/processor.

As used herein, the term "communication resources" may refer to hardware and/or firmware for electronic information transfer. Wireless communication resources may include hardware to transmit and receive signals by radio and may include various protocol implementations e.g. the 802.11 standard described in the Institute of Electronics Engineers (IEEE) and Bluetooth™ from the Bluetooth Special Interest Group of Kirkland Wash. Wired communication resources may include Universal Serial Bus (USB); High-Definition Multimedia Interface (HDMI) or other protocol implementations. The apparatus may include communication resources for communication with a peripheral device.

As used herein, the "heating system (being) arranged in fluid communication with the flow path" may refer to an interaction or exchange between the heating system and the flow transmitted by the flow path, such as (but not limited to) between components of the heating system, such a heating coil, and air, precursor, solid materials and/or aerosol comprised in the flow. For example, the heating system is in fluid communication with the flow path if a heating element such as a coil is located in the flow path. In this case, the heating element heats the flow, and vice versa the flow may have a cooling effect on the heating element.

As used herein, the term "network" or "computer network" may refer to a system for electronic information transfer. The network may include one or more networks of any type, which may include: a Public Land Mobile Network (PLMN); a telephone network (e.g. a Public Switched Telephone Network (PSTN) and/or a wireless network); a local area network (LAN); a metropolitan area network (MAN); a wide area network (WAN); an Internet Protocol Multimedia Subsystem (IMS) network; a private network; the Internet; an intranet.

As used herein, the term "peripheral device" may include electronic components peripheral to an apparatus. The peripheral device may comprise electronic computer devices including: a smartphone; a PDA; a video game controller; a tablet; a laptop; or other like device.

As used herein, the term "storage portion" may refer to a portion of the apparatus adapted to store the precursor.

As used herein, the term "delivery system" may refer to a system operative to deliver, by inhalation, aerosol to a user. The delivery system may include a mouthpiece or an assembly comprising a mouthpiece.

As used herein, the term "flow path" may refer to a path or enclosed passageway through the apparatus, through which the user may inhale for delivery of the aerosol. The flow path may be arranged to receive aerosol.

As used herein, the term "flow" may refer to a flow in the flow path, and may include air, which may be induced into the flow path due to an inhalation through the flow path and/or aerosol.

As used herein, the term "inhale" may refer to a user inhaling (e.g. due to an expansion from their lungs) to create a pressure reduction to induce flow through the flow path.

As used herein, the term "atomizer" may refer to a device to form the aerosol from the precursor. The atomizer may include a heating system, ultrasonic or other suitable system.

As used herein, the term "property of electrical energy through the heating system" or "measured property of electrical energy" may refer to or be based on one or more of the: current; electrical potential; power; phase; other related property, of the electrical energy through and/or over the heating system (e.g. one or more electrically resistive elements thereof) or a component associated therewith (e.g. a resistor, that may include a shunt resistor, arranged in series with or parallel to the heating system or with other suitable operative arrangement). It also includes a like property measured through a component different from but arranged in operative proximity to the heating system (i.e. to provide a representative measure of the electrical energy through the heating system) such as a temperature sensor, which may operate based on temperature dependent electrical resistance. The property may refer to the time dependency of the property of the electrical energy.

As used herein, the term "property related to the flow" or "property of the flow" may refer to one or more of the following associated with the flow in the flow path: a flow rate (e.g. volumetric or mass) of aerosol and/or air; duration of an inhale; start of an inhale; end of an inhale; intensity of an inhale; flow velocity; a quantity of flow (e.g. volumetric or mass), including one or more components of the aerosol of the flow (e.g. nicotine, caffeine) and/or air, which may be associated with an inhale.

As used herein, the term "characteristic of the second order time derivative" in respect of the measured property of the electrical energy may include/refer to one or more of the following features: a stationary point, e.g. a maximum or minimum; other point of inflection, including a saddle point; a period associated with a stationary point, which may be in respect of a baseline value; a period between stationary points, which may be immediately consecutive or separated, e.g. by a period of baseline; a step or other discontinuity; a rise or fall from baseline, e.g. for a pulse; a position associated with an amplitude of a pulse, e.g. 25% of amplitude. The various points may be characterised in respect of magnitude and/or position in time.

Referring to FIG. 1, embodiment aerosol generation apparatus 2 includes a power supply 4, for supply of electrical energy. The electrical energy may be supplied to an atomizer 6 and/or electrical circuitry 8. The power supply 4 may include an electric power supply in the form of a battery and/or an electrical connection to an external power source. The apparatus 2 may include a precursor transmission system 10 to transmit precursor to the atomizer 6 for formation of aerosol therefrom. A delivery system 12 delivers the aerosol to a user.

Figure 2:
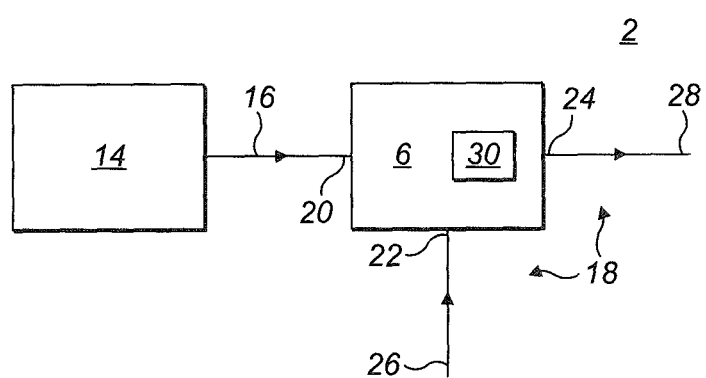
FIG. 2 is a schematic diagram showing embodiment componentry of the system of FIG. 1.

Referring to FIGS. 1 and 2, embodiment aerosol generation apparatus 2 includes the precursor transmission system 10 having a storage portion 14 for storage of the precursor. The storage portion 14 may be arranged as a reservoir (not shown) or other suitable arrangement portion depending on the physical state of the precursor. The precursor transmission system 10 includes a transmission unit 16 to transmit the precursor from the storage portion 14 to the atomizer 6. The transmission unit 16 may include one or more of: an absorbent member (e.g. cotton) arranged for transmission by capillary action; a conduit; a valve; a pumping system, which may include an electrically operated pump.

In an embodiment, which is not illustrated, the precursor transmission system 10 may be omitted. In such an embodiment the precursor may be arranged as a consumable pod (e.g. as a liquid or gel), wherein an atomizer includes a heated receptacle for the pod.

The delivery system 12 includes a flow path 18 to transmit aerosol from the atomizer 6 to a user. The atomizer 6 includes a precursor inlet 20. The atomizer 6 includes a flow inlet 22 and an outlet 24 of the flow path 18 for passage of flow through the atomizer 6. In an embodiment, which is not illustrated, the flow path 18 receives aerosol from the outlet 24 and does not pass through the atomizer 6.

The flow path 18 includes an inlet 26, which may be arranged through a housing of the apparatus 2. The flow path 18 includes an outlet 28 for delivery of the aerosol and inlet flow to the user. The outlet 28 may be arranged as a mouthpiece or other suitable delivery member.

The atomizer 6 includes a heating system 30, which may be arranged as one or more electrically resistive heating elements (not shown). A heating element may be arranged as a wire or filament. A heating element may be operatively connected to the precursor transmission unit 16 to heat precursor of the transmission unit 16. The one or more heating elements may be arranged within and/or in fluid communication with the flow path 18, e.g. to be cooled by said flow.

In an embodiment, which is not shown, a cartomizer integrates a storage portion 14 and transmission unit 16 of the transmission system 10 and heating system 30 in a common housing. The cartomizer including a predetermined amount of the precursor.

The circuitry 8 regulates electrical energy from the power supply 4 to the heating system 30. Proximal a heating element the precursor may be converted to a supersaturated vapour, which subsequently condenses to form an inhalable aerosol. As precursor is converted to aerosol, it is replaced by further precursor supplied by the transmission unit 16, e.g. by a pumping action, until the storage portion 14 is spent.

The electrical energy supplied to the heating system 30 may be controlled with the circuitry 8 by one of the following or other like circuitry: pulse width modulation (PWM) via an electrically operated switch, or by other suitable means, e.g. by chopping of an alternating current waveform; a direct current (DC): DC converter, such as a Buck converter; a linear regulator.

The circuitry 8 implements some form of control of the temperature of the heating system 30, e.g. by closed loop control. Depending on the embodiment, the control may comprise regulating one of the: electrical potential; current; power; temperature; other related quantity to remain at a target value through (or over) the heating system 30.

Since the heating system 30 may include resistive elements arranged within the flow path 18, inhalation through the flow path has the effect of cooling the heating system 30. Said cooling influences the electrical resistance of the resistive elements, and therefore the degree of cooling can be representative of the intensity of the user inhalation, i.e. the flow rate through the flow path, and since the amount of precursor delivered as an aerosol from the transmission unit 16 may have a dependency on the intensity of the inhalation, the resistance can be used to determine the property of the flow as defined herein.

In embodiments wherein the voltage is regulated as constant over the heating system 30, the change in electrical current to maintain a constant voltage during an inhalation can be representative of the intensity of the inhalation.

In embodiments wherein a temperature of the heating system is regulated at a target temperature, e.g. by proportional-integral-derivative (PID) or other like control algorithm, the power (or other related quantity such as electrical current) to maintain the target temperature during an inhalation can therefore be representative of the intensity of the inhalation.

A temperature of the heating system 30 may be determined by measuring the electrical resistance as described above and by implementation of an empirically determined relationship between electrical resistance and temperature. Alternatively, the circuitry may implement a dedicated temperature sensor arranged in operative proximity to the heating system 30.

It will be understood that the examples presented in the subsequent embodiments may be adapted for the various aforementioned forms of heating system 30 control.

The circuitry 8 may comprise a trigger (not shown) to detect when aerosol formation is required. The circuity 8 may effect the supply of electrical energy to the heating system 30 upon the determination of triggering of the trigger. The trigger may detect when a user action suggests aerosol formation is required. Such a request may be implicit, such as via inhalation, or explicit, such as via a button press. The trigger may comprise an actuator being actuated by physical contact (e.g. a vaping button), including by a digit of a hand of the user. Examples include a button or a dial. The trigger may comprise an inhalation sensor operable to detect user inhalation through the flow path 18. The inhalation sensor may comprise a flow meter or a pressure sensor operable to determine flow pressure, including by capacitive sensing of a pressure respondent displaceable diaphragm.

Figure 3:
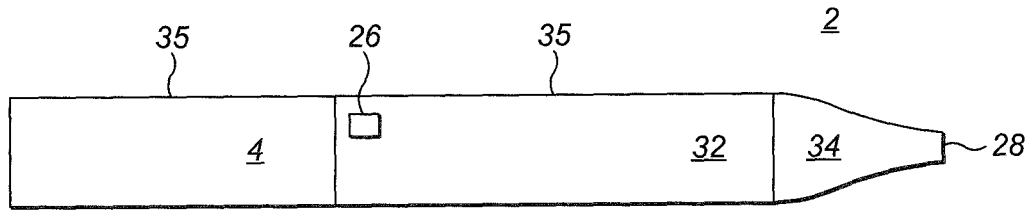
FIG. 3 is a schematic diagram showing an embodiment of the system of FIG. 1.

Referring to FIG. 3 an embodiment arrangement of the apparatus 2 comprises: a cartomizer 32 interconnecting a power supply 4 and a mouthpiece 34. The mentioned components may be connected in a modular fashion, including by bayonetted or threaded connection types or other suitable connection. The apparatus 2 is geometrically elongated along a longitudinal axis. The mentioned components can be arranged in the form of an elongated cylindrical shape, so as to replicate that of a cigar or cigarette. In embodiments, which are not illustrated, the mentioned components are alternatively arranged; e.g. the atomizer may be arranged separable from a storage portion. One or more of the mentioned components may be arranged in a common housing 35.

Referring to FIGS. 1-5, an electrically operated aerosol generation system 36 for generation of an aerosol may implement features of any of the preceding embodiments or other embodiments disclosed herein. The system 36 is configured to generate an aerosol from an aerosol-forming precursor and comprises the heating system 30 to heat said precursor to generate the aerosol. The flow path 18 includes the inlet 26 for air inlet and the outlet 28 for delivery of the aerosol and inlet air. The heating system 30 is arranged in fluid communication with the flow path 18, including to receive flow 50 of the flow path.

Electrical circuitry 8 at block 38 determines (e.g. measures) a property of electrical energy through the heating system 30. The dependency of the property with respect to time may be determined. Examples of suitable properties are as disclosed herein, which include current or voltage. As used herein, the term "determining a property of electrical energy through the heating system" or "a property of electrical energy through the heating system" may refer to direct measurement of the property of the electrical energy through the heating system and/or a representative measurement of the property of the electrical energy elsewhere in the circuitry associated with the heating system (e.g. a resistor in parallel or series with the heating system, which may include a shunt resistor).

The electrical circuitry 8 at block 40 determines a second order time derivative of the determined property of the electrical energy through the heating system 30. As used herein, "determination of a second order time derivative" or "based on the second order time derivative" (or a like term) may include a representative quantity without explicit formulation, as well as with explicit formulation. Exemplary derivation methods for the second order derivative will be provided.

Electrical circuitry 8 at block 42 determines a characteristic of the second order time derivative, examples of which are as disclosed herein, which include features such as a peak to peak value of maxima and minima. The term "characteristic of the second order time derivative" is to be understood as not limited to a single feature; e.g. it may comprise said peak to peak value and a time of a maximum; further examples will be provided.

Electrical circuitry 8 at block 44 processes the determined characteristic of the second order time derivative to determine the property related to the flow. Examples of the property related to the flow are as disclosed herein, which include an amount of one or more components of the aerosol dispensed during a user inhale through the flow path 18.

In embodiments, the property related to the flow may be determined based on a relationship between the property related to the flow and the characteristic of the second order time derivative; e.g. the relationship may be based on empirical data, examples of which will be provided. In other embodiments, which are not illustrated, the circuitry 8 may implement alternative procedural steps, e.g. a fixed operation is performed on the characteristic.

Electrical circuitry 8 at optional block 46 outputs the determined property related to the flow, which may include providing instructions to a user interface to display the determined property and/or to store said property, examples of which will be provided.

In accordance with the definition of circuitry 8 herein, it will be understood that the process blocks 38-46 (or any other block associated therewith and like process steps of other embodiments disclosed herein) may be executed centrally on the apparatus 2 and/or distributed on other circuitry associated with the system 36, e.g. a peripheral device 48, which may be implemented as a smartphone.

The procedural steps exemplified by the blocks of FIG. 4 will now be described in more detail, commencing with block 38. The circuitry 8 for determination of the property of electrical energy through the heating system 30 may be implemented in various manners.

[Determination of Property of Electrical Energy Through the Heating System]

Figure 6:
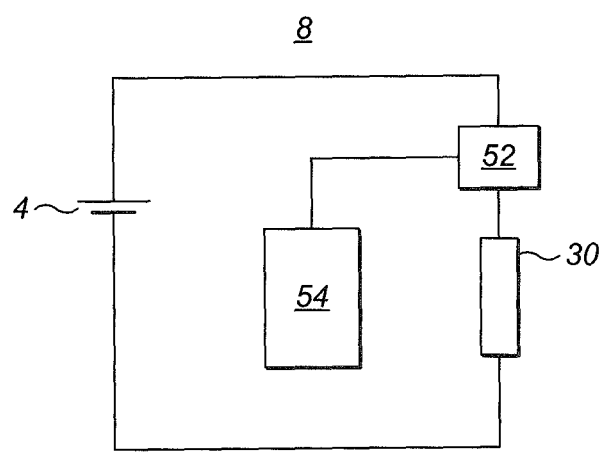
FIG. 6 is a schematic diagram showing embodiment circuitry of the system of FIG. 1, the circuitry for determining the property of the electrical energy through a heating system.

Referring to FIG. 6, the circuitry 8 implements a circuit for determining the property of the electrical energy through the heating system 30. The circuitry 8 includes a measurement unit 52 to measure a property of the electrical energy through or over a heating element of the heating system 30. The measurement unit 52 may be implemented as a resistor (e.g. a shunt resistor, not shown) arranged in series with the heating system 30 and a potentiometer (not shown) arranged to measure the electrical potential over the resistor. The electrical potential over the resistor may be converted to current by division of the resistance. Accordingly, the property of the electrical energy through the heating system 30 may be based on current and/or electrical potential. A processor 54 determines the property of the electrical energy based on a signal from the measurement system 52.

In embodiments, which are not illustrated, the measurement unit may have other implementations, e.g. a potentiometer arranged to measure the electrical potential directly over the heating system or other property that may include phase or power. Moreover, the processor may implement elements of the measurement unit, e.g. the potentiometer as an algorithm and/or a combinational logic circuit. The processor may also implement elements of a control system to control the electrical energy to the heating system, e.g. for PWM control, or DC:DC conversion. The processor 54 may implement determination of the second order time derivative of the variation of the property of the electrical energy through the heating system 30 and subsequent determination of a property related to the flow as will be discussed.

The heating system 30 may comprise a single or multiple heating elements. The material of the heating element may be selected to have a high temperature coefficient of resistance $\alpha$, e.g. 30-90×$10^4$, such as Nickel. In the embodiments, the or each heating element of the heating system 30 may be heated to a range to cause vaporisation of the precursor without combustion of the precursor, e.g. to 150-350° C.

Figure 7:
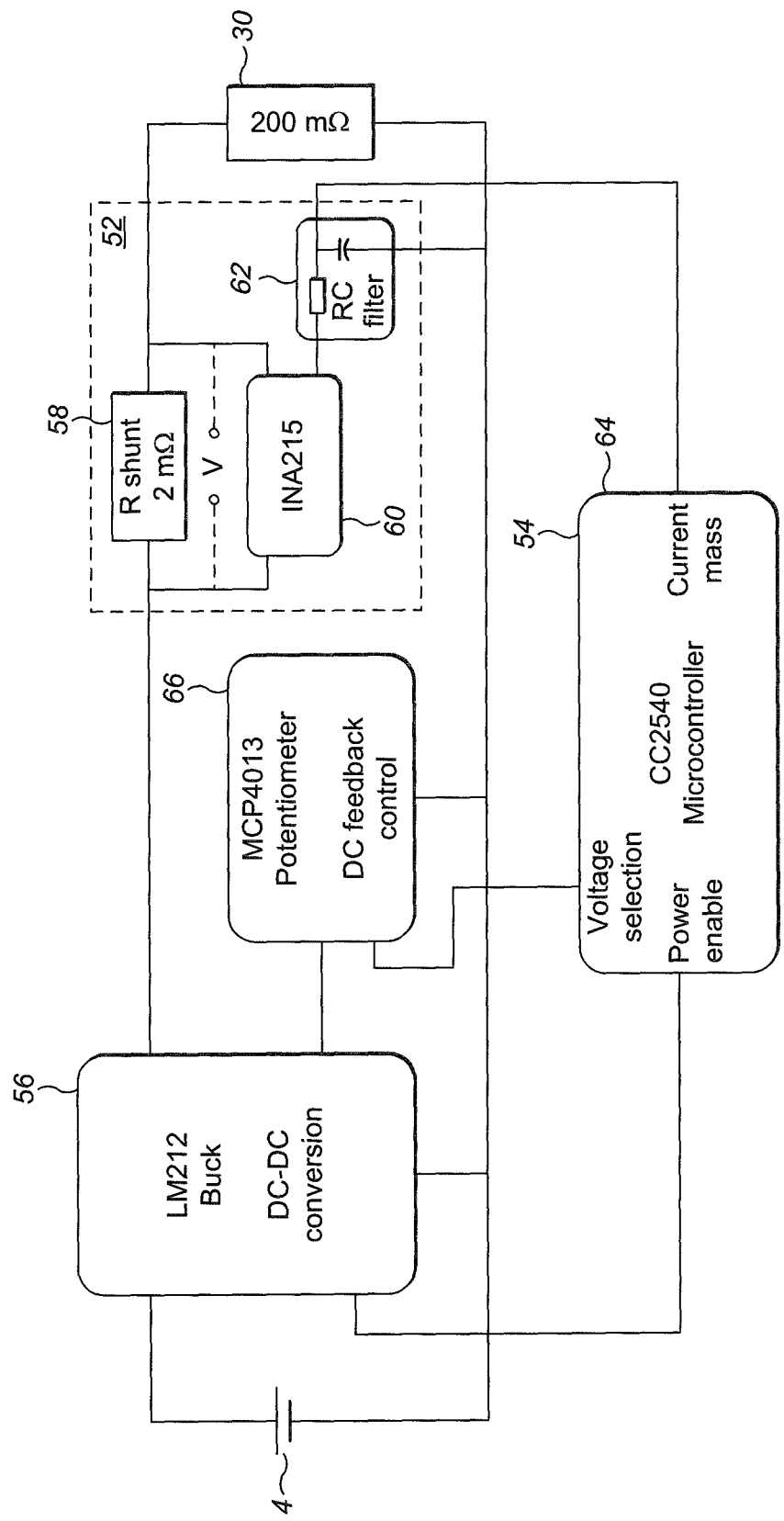
FIG. 7 is a schematic diagram showing a more detailed implementation of the circuitry of FIG. 6.

Referring to FIG. 7, which is a more detailed implementation of the circuitry 8 of FIG. 6, the circuitry 8 includes exemplary componentry for illustrative purposes. The measurement system 52 is implemented as 2 m$\Omega$ shunt resistor 58, which is arranged in series with the heating system 30. The heating system 30 has a 200 m$\Omega$ electrically resistive load. An amplifier 60 amplifies the electrical potential over the shunt resistor 58. The amplifier is an INA215 by Texas Instruments with a gain of 50. Filter 62 is arranged to filter the amplifier 60 output, e.g. to remove noise including spurious modes. The processor 54 is implemented as a microcontroller 64. The microcontroller 64 is a CC2540 by Texas instruments.

A DC-DC converter 56 (which in the embodiment is implemented as a buck converter) is arranged to provide a stabilised continuous voltage from the power supply 4. The DC-DC converter is a LM212 Buck by Texas Instruments. The power supply 4 has a nominal supply of 3.7 V. The DC-DC converter 56 outputs a continuous voltage of 2.5V, but may be controlled to 1.9-2.75V. The microcontroller 64 provides control of the DC-DC converter 56. A potentiometer 66 is arranged to provide a reference voltage to the microcontroller 64 and DC-DC converter 56. The potentiometer 66 is an MCP4013 by Microchip. The voltage is controlled by the microcontroller 64, which sets the reference voltage of the potentiometer 66.

Since the resistance of the shunt resistor 58 is relatively constant, the electrical potential over the shut resistor 58 may be converted to current by division of said resistance. Accordingly, the property of the electrical energy through the heating system 30 may be based on current and/or electrical potential, or other quantities that may be derived therefrom, such as power.

It will be understood that the second order time derivative of the determined property of the electrical energy through the heating system 30 is relatively independent of the specific implementation (e.g. resistances) of components of the circuitry 8. Moreover, said independence may reduce any effect of variations of electrical componentry (e.g. manufacturing tolerances) implementing the same circuitry 8, e.g. for batches of the same apparatus 2.

The filter 62 may be implemented as a low pass filter, e.g. a resistor-capacitor (RC) filter. The pass frequency may be below 20 Hz. In an embodiment, the filter (or an additional filter) is implemented as a digital filtering algorithm (or logic circuit) optionally arranged on the processor 54. A digital filter can advantageously be field configured by the processor 54. The filter may implement a smoothing algorithm to increase signal-to-noise ratio with minimal distortion; a suitable implementation includes a Savitzky-Golay filtering algorithm. In an embodiment, the filter is selected to filter out oscillations due to bubbles in the reservoir or other fluctuations.

[Example of Measured Property of Electrical Energy Through Heating System]

Referring to FIGS. 8-11, line 72 represents the time dependency of electrical current through the heating system 30 when measured using the embodiment circuitry 8 shown in FIG. 6 or 7. A similar time dependency may be obtained when measuring other properties of the electrical energy through the heating system; examples include power.

In the embodiment (as discussed previously), a constant electrical potential is maintained over the heating system 30. The electrical current through the heating system 30 causes the or each heating element thereof to heat up. The temperature increase of the heating element causes a resistance increase, which due to regulation of a constant electrical potential has a resultant effect of decreasing the electrical current through the heating system 30.

Figure 8:
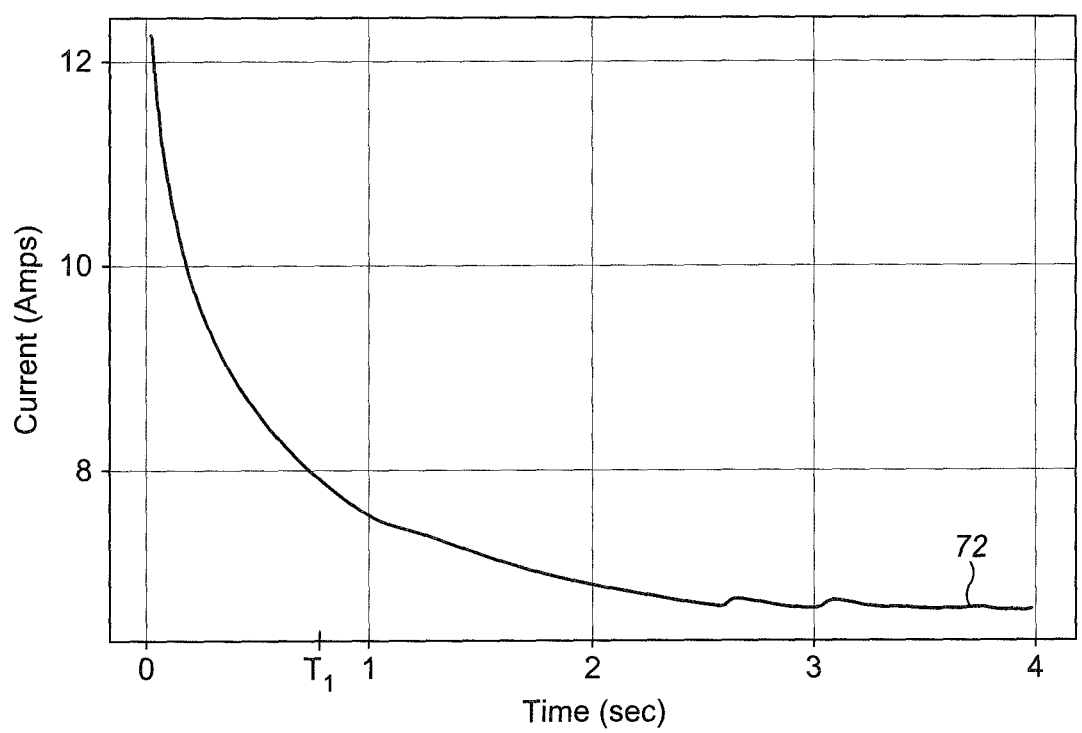
FIG. 8 is a graphical diagram showing an example of electrical current through an electrical heating system of the embodiment circuitry of FIG. 6 or 7.

Referring to FIG. 8, at $T_0$ the electrical energy is applied to the heating system 30. It can be observed that the electrical current through the heating system 30 decreases in an exponential manner. This is due to the heating system 30 exhibiting a substantial initial temperature increase as it is heated, followed by convergence to a constant temperature. Since the electrical resistance is proportional to the temperature, to maintain the constant electrical potential, the current exhibits corresponding exponential decay.

In an embodiment, which is not illustrated, the circuitry 8 implements a constant current source, which is arranged to maintain a constant current over the heating system 30. As the resistance of the heating element increases, the electrical potential over the constant current source increases, thus the electrical potential exhibits a similar time dependency as for the electrical current of the preceding embodiments. A similar time dependency may be obtained when measuring the power over the heating system or other representative quantity. It will thus be understood that the relationship between the property of electrical energy through the heating system 30 and the property related to the flow of the flow path may apply to various electrical quantities that are selected based on the implementation of the circuitry 8.

When a user inhales through the flow path 18, heat is dissipated from the heating system 30 to the flow 50, e.g. by convective heat transfer of thermal energy from the heating element to the flow stream. The heat dissipation of the heating system 30 is thus related to the flow 50 through the flow path 18. Since the temperature of the heating element is related to its electrical resistance, the temperature thus influences the property of the electrical energy through the heating system 30 (e.g. the electrical potential over the heating system 30 or current through the heating system 30 depending on the implementation of the circuitry 8). The electrical energy through the heating system 30 is thus related to various properties of the flow 50 in the flow path 18 as will be discussed.

Figure 10:
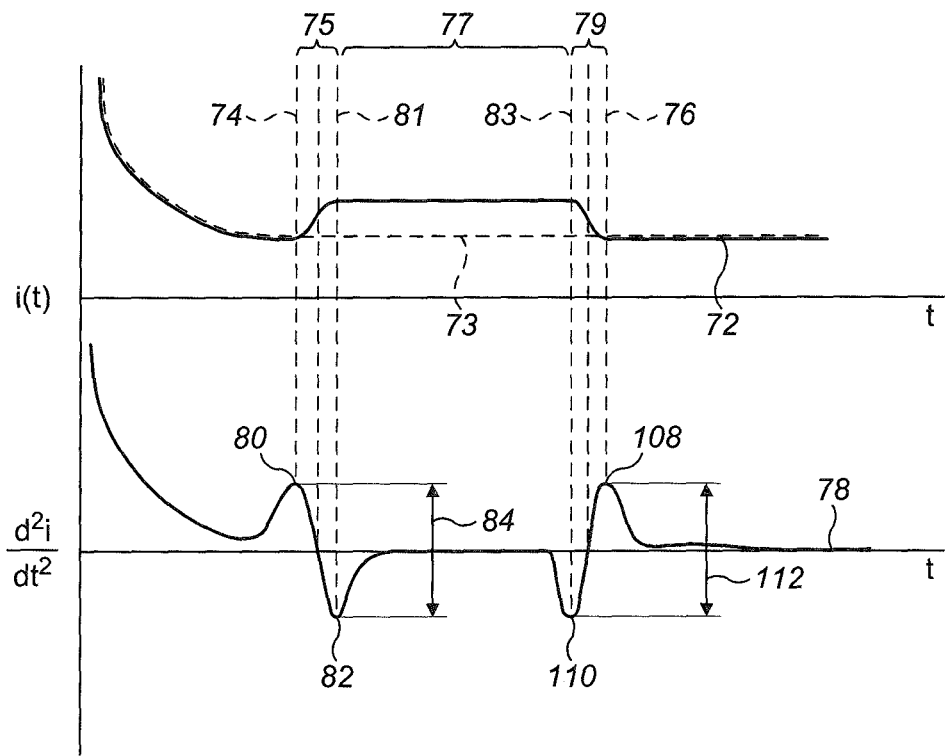
FIG. 10 is a graphical diagram showing an example of electrical current and a second order time derivative thereof through an electrical heating system of the embodiment circuitry of FIG. 6 or 7, with the effect of a user inhale through a flow path of the system of FIG. 1 shown in detail.
Figure 11:
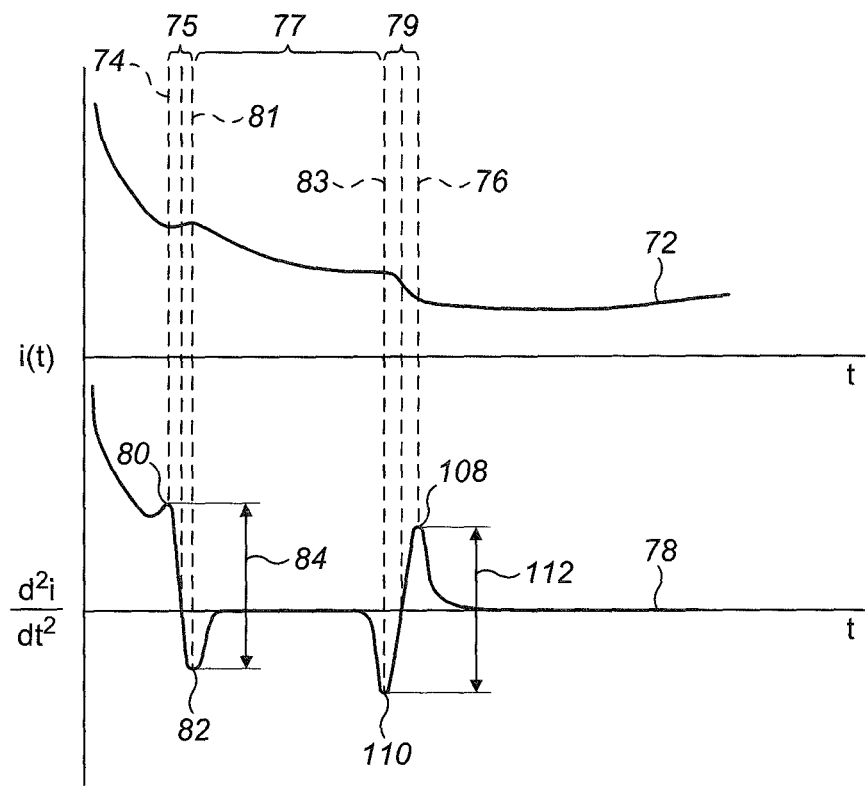
FIG. 11 is a graphical diagram showing an example of electrical current and a second order time derivative thereof through an electrical heating system of the embodiment circuitry of FIG. 6 or 7, with the effect of a user inhale through a flow path of the system of FIG. 1 shown in detail, wherein the inhalation is initiated earlier than as shown in FIG. 10.

Referring to FIGS. 10 and 11, the influence of a user inhale through the flow path 18 on the electrical current is more clearly illustrated, wherein line 72 shows the current during an inhalation and line 73 shows the current in absence of an inhalation. Line 78 is the second order time derivative of line 72. In particular at reference lines 74 and 76 a user inhalation is initiated and terminated respectively. It can be seen that the initiation of the inhale causes an initial oscillation 75 in the current followed by a period of increased current 77 and an oscillation 79 at termination. The effect is more pronounced in the second order time derivative 78 of the current. At line 81 the initial oscillation 75 ceases to have an effect on the second order time derivative 78. At line 83 the termination oscillation 79 initiates an effect on the second order time derivative 78.

Figure 9:
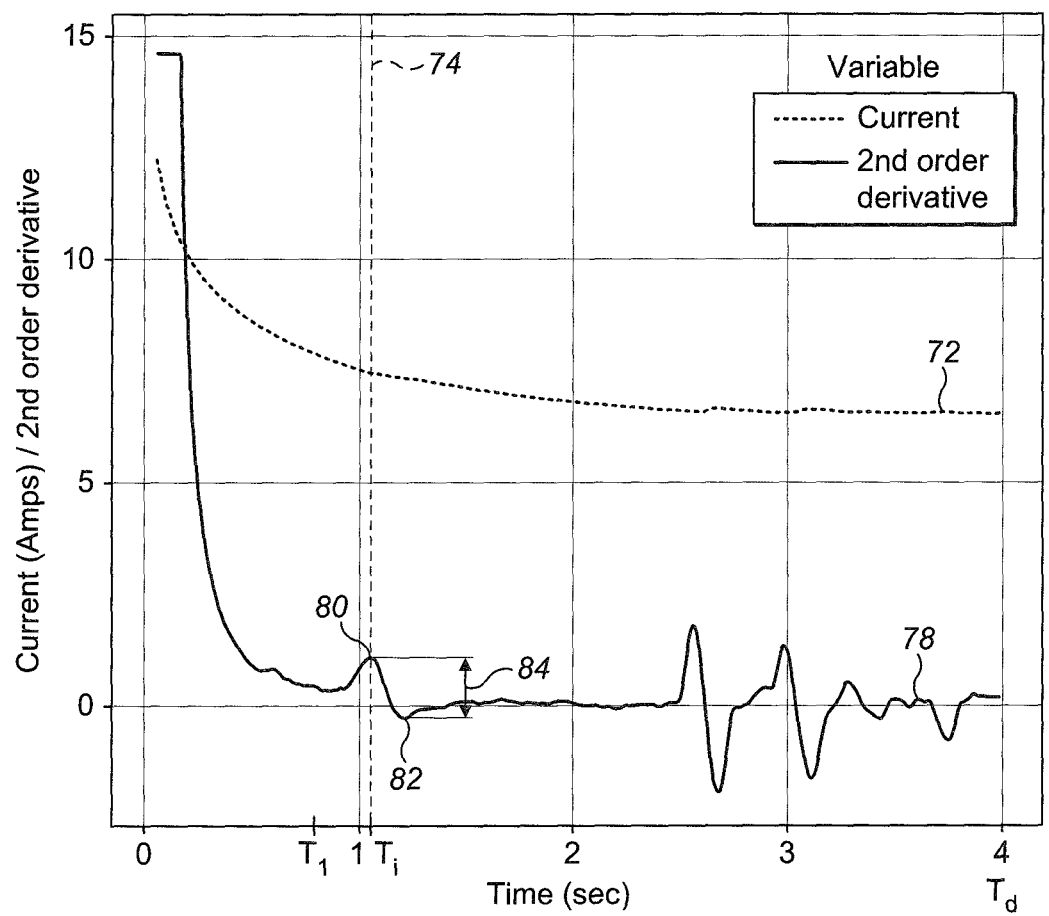
FIG. 9 is a graphical diagram showing the electrical current of FIG. 9 and a second order time derivative thereof.

Referring to FIGS. 8 and 9, the current decreases from an initial magnitude of over 12 amps to: 8.5-7.5 amps between 0.5 and 1 seconds; 7.5-7 amps between 1 and 2 seconds; a nominal value of 6.5-7 amps after about 2 seconds. With the nominal value as a reference, current thus falls by over 70% in the first 0.5 seconds. It may be preferable to measure the effect of the user inhale on the current through the heating system 30 following 0.5 seconds, wherein the current has stabilised and the effect of the oscillations due to inhalation may appear more pronounced.

It is thus desirable that the user inhale occurs following the supply of a predetermined amount of electrical energy and/or with some preheating of the heating element to enable the effect of the initiation of the user inhale to be captured.

A used herein "nominal value" may refer to a normal operating value of a signal of the electrical energy, which the circuitry 8 may be designed to operate with. Nominal may refer to a value that the signal converges to or about.

Figure 12:
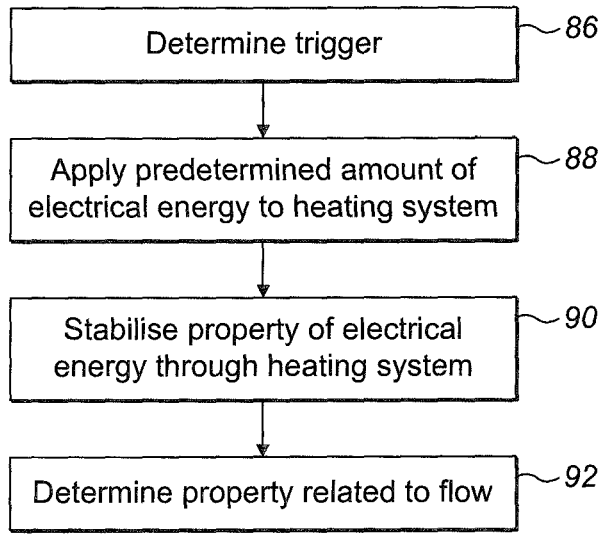
FIG. 12 is a flow diagram showing embodiment processes implemented by the system of FIG. 1 to determine a property of flow through said system, wherein the property is stabilised by a predetermined amount of electrical energy prior to determination of said property.

Referring to FIG. 12, circuitry 8 implements an embodiment process for stabilising a property of the electrical energy through the heating system 30. The process may be implemented in combination with the embodiment process illustrated in FIG. 4, or another embodiment disclosed herein. At block 88 the circuitry 8 applies a predetermined amount of electrical energy to the heating system 30. At block 90 the predetermined amount of electrical energy stabilises the property of electrical energy (e.g. the current in the exemplary embodiment) through the heating system 30. At block 92 the circuitry 8 determines a property related to the flow 50 of the flow path 18 based on the property of the electrical energy through the heating system 30 subsequent to the applied predetermined amount of electrical energy, i.e. with said property stabilised, examples of which will be provided.

Inhalation (which may include initiation of inhalation) following application of the predetermined amount of electrical energy may be ensured by implementing one or more embodiment modes of operation of the circuitry 8. In an embodiment, at block 86, the predetermined amount of electrical energy is applied upon determination of a trigger as previously described. The trigger may comprise an actuator actuated by physical contact (e.g. a vaping button), including by a digit of a hand of the user. The electrical circuitry 8 may implement the actuator with electrical energy applied to the atomizer 6 for the duration of the actuation. It has been found that with such an actuator most users initiate inhalation after 0.5 or 1 seconds of actuation. Thus, the circuitry 8 can be specifically configured to apply the predetermined amount of electrical energy before 0.5-1 second. Said configuration can be implemented by the control system of the processor 54 for regulation of electrical energy to the heating system 30 (e.g. the DC:DC converter or PWM based control system applies the predetermined amount of electrical energy in the first 0.5-1 second or other suitable time period $T_1$).

In other embodiments, the circuitry 8 implements the trigger as a motion sensor or facial recognition sensor (e.g. a camera with image processing) to determine intent to initiate an inhalation.

In an embodiment, the circuitry 8 may implement enabling of inhalation through the flow path 18 only when the heating system 30 is heated to a predetermined temperature and/or the current is within a particular range of the nominal value (e.g. ±40% or ±25%). The circuitry 8 may enable inhalation by means of an electrically operated value or other flow regulation device.

Referring to FIGS. 8 and 9, the circuitry 8 applies the predetermined amount of electrical energy over the first time period $T_1$. Initiation of the inhale through the flow path 18 is indicated by line 74 at $T_i$, which occurs after $T_1$ and during a subsequent time period. The circuitry 8 thus determines the property related to the flow through the flow path as will be discussed. The circuitry 8 may be configured to apply the predetermined amount of electrical energy over a $T_1$ duration of 0.3-2, or 0.6-1.5 or less than 1 or 0.5 seconds.

Whilst it is preferable to ensure $T_i$ occurs after the predetermined amount of electrical energy has been applied, in an embodiment the property of the flow is based on an oscillation at termination of the inhalation (examples of which will be provided); thus, in some examples, the $T_i$ occurs before the predetermined amount of electrical energy has been fully applied.

The predetermined amount of electrical energy may be 20, 25 or 30 Joules (each ±40% or ±25% or ±10%). In the embodiment implementations of FIGS. 6 and 7, the predetermined amount of electrical energy can include 2.5V applied for $T_1$ (as defined by the previous ranges).

The predetermined amount of electrical energy may be to preheat a heating element of the heating system 30 to a predetermined temperature range from which may be cooled during said inhale. The predetermined temperature range may be selected to cause vaporisation of the precursor without combustion of the precursor, e.g. to 150-350° C. or 200-250° C. The temperature of the heating element may be determined by various implementations, which include: resistance of the heating system; a dedicated temperature sensor; empirical data (e.g. a particular amount of energy is known to effect an experimentally determined temperature range).

The predetermined amount of electrical energy may be to stabilise the property of the electrical energy through the heating system 30 to ±25% or ±40% of the nominal value. In the example the nominal value of the current may be taken as 6.5 amps, thus +40% or +25% equates to 9.1 amps and 8.1 amps respectively, 8.1 amps occurs during $T_1$. The same ranges may be applied to other properties (e.g. electrical potential) of the electrical energy through the heating system 30 in other embedment implementations of the circuitry 8.

The predetermined amount of electrical energy may be to stabilise the property of the electrical energy through the heating system so that oscillations caused by the user inhale through the flow path can be extracted and processed. The oscillations may include those in a first or second order time derivative as will be discussed.

The specific amount of electrical energy to achieve the aforementioned stabilisation will depend on the implementation of the apparatus 2, which includes implementation of: the circuitry 8; heating system 30, including the resistance of the heating element; the flow path. Thus, it will be understood that the specific amount of electrical energy may be determined based on empirical data.

Referring to FIG. 9, after approximately 2.5 seconds the current 72 exhibits notable oscillation (which can be more clearly seen in the corresponding second order time derivative 74). The oscillation is electrical noise caused by overheating of the heating element of the heating system 30. It may therefore be desirable to configure the circuitry 8 such that the user inhale through the flow path 18 occurs prior to the electrical noise, such that the electrical noise may not interfere with measurement of the inhale. This may be achieved by application of the predetermined amount of electrical energy as close to initiation of the user inhale as possible.

Since the second order time derivatives are particularly vulnerable to interference as the electrical energy through the heating system 30 decreases from its initial value to the nominal value, it may be desirable to implement circuitry 8 that applies the predetermined amount of electrical energy in combination with processing of the second order time derivative to calculate the property of the flow, examples of which will be provided.

However, in some embodiments, the property of the electrical energy through the heating system 30 without numerical differentiation may be processed to calculate the property of the flow, examples of which will be provided.

[Determination of Second Order Time Derivative]

Referring FIGS. 4, and 9-11, the circuitry 8 at block 40 determines a second order derivative with respect to time of the determined property of the electrical energy through the heating system 30.

Determination of the second order time derivative may be implemented by an algorithm (or logic circuit), which may be arranged on the processor. The finite difference method (e.g. Newton's difference quotient, symmetric difference or a higher-order method), or other methods such as differential quadrature, may be implemented. Derivation of the derivative may also be determined by electrical componentry, e.g. a finite difference method is implemented by a capacitor arranged to introduce a delay in the property of the electrical energy through the heating system 30 and a differential amplifier to determine a derivative from the property of the electrical energy and delayed property of the electrical energy.

It will be understood that explicit determination of the second order time derivative is not required, e.g. when implementing a finite difference method, the small change in time may not be divided by if the change in time between the function sampling points remains constant. In embodiments explicit formulation of the derivative is implemented.

[Determination of Characteristic Feature of the Second Order Time Derivative]

Figure 4:
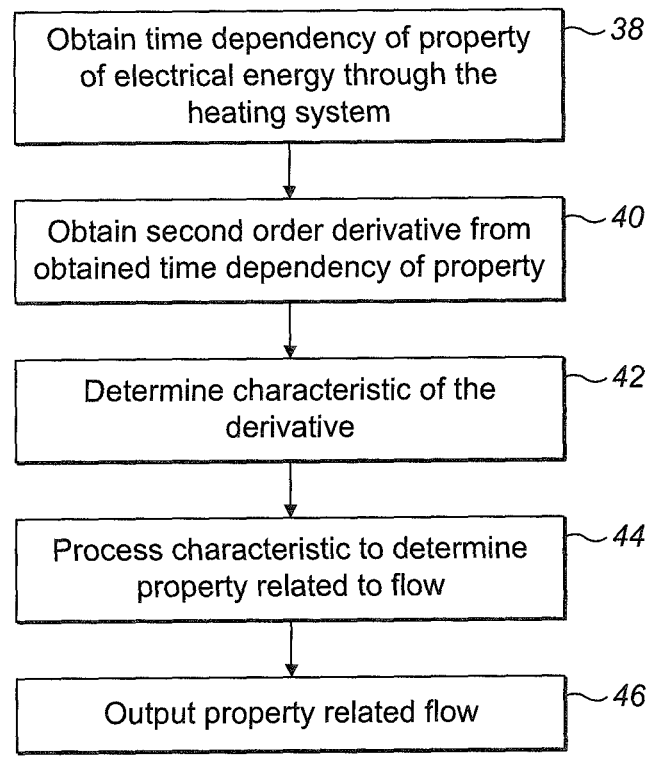
FIG. 4 is a flow diagram showing embodiment processes implemented by the system of FIG. 1 to determine a property of flow through said system.

Referring to FIG. 4, at block 42 the characteristic feature of the second order time derivative may be extracted by the circuitry 8, including by an algorithm (or logic circuit) arranged on the processor.

The specific characteristic to be extracted may depend on the particular relationship that is implemented to determine the property of the flow of the flow path 18, examples of which will be provided.

The relationship may require extraction of a class comprising one or more features (referred to as input values), of the second order derivative, all of which are encompassed by the term "characteristic feature of the second order time derivative".

It will be understood that depending on the specific class to be extracted, various processes for feature extraction may be implemented, e.g. stationary points or initial rises/falls from baseline can be determined via comparison of a magnitude of a data point to an adjacent data point, a peak to peak amplitude of adjacent maxima and minima or an amplitude of a maximum or minimum may subsequently be determined.

[Determine Property of Flow]

Referring to FIG. 4, at block 44 the determined characteristic feature of the second order time derivative is processed to determine the property of the flow. Processing may include the implementation of a particular relationship to determine the property of the flow 50 of the flow path 18. The relationship can be implemented by the circuitry 8, including by an algorithm (or logic circuit) arranged on the processor.

As used herein the term "relationship" may refer to a relationship between the property of the electrical energy through the heating system 30 and the property of the flow of the flow path 18. The relationship may be an empirical relationship, e.g. one obtained by experimentally obtained data. The empirical data can be stored on a memory associated with the circuitry 8. Thus, in embodiments, an "empirical relationship" may also be referred to as a "stored relationship", and the terms "empirical" and "stored" may be used interchangeably. The relationship may include a mathematical function, with one or more input variables and an output variable. The output variable comprises the property of the flow. The one or more input variables comprises the previously described class of one or more characteristics.

A range of suitable output values is provided under the definition of the "property related to the flow". A range of suitable input values (i.e. a class) is provided under the definition of the "characteristic of the second order time derivative", and/or other features of the electrical energy through the heating system 30.

The herein defined relationships may be better understood in view of the following example:

[Example 1]

An exemplary embodiment that implements one or more features of the previously described embodiments, or another embodiment disclosed herein, will now be provided.

The relationship provided in equation (1) may be implemented by circuitry 8 to determine the property of the flow, $$M = A.I^2 + B.I + C.T_i + D.T_d + E.V - F \qquad (1)$$

wherein the output value is the mass M of aerosol present in a user inhale through the flow path 18. Coefficients A-F are determined by regression of empirical data and have the respective values: 0.5965; 0.1223; 0.002088; 0.0004042; 0.05651; 134.0. Referring to FIG. 9, the input values comprise: a peak to peak magnitude 84, which is denoted as "I"; the constant voltage maintained over the heating system 30, which is denoted as "V" in mV; the duration of the electrical energy applied to the heating system "$T_d$" in mSec; the initiation time of the inhalation "$T_i$" in mSec. Since the voltage Vis generally a constant, E and V may be replaced as a single coefficient.

The above relationship will now be utilised by way of example:

The input values include: a voltage V of 2.51 V; a duration of the electrical energy $T_d$ of 3.987 seconds; $T_i$ of 1.035 seconds; an intensity I of 1.370. The above relationship determines M as 12.9 mg with an experimental error of ±2-3%. The experimentally obtained value of M was obtained by measuring the depletion of a storage portion containing the precursor. A user inhale through the flow path was replicated by a pump with a calibrated representative flow rate of 18.33 ml/s.

The amount of individual components of the aerosol, e.g. nicotine, can be determined based on their concentration in the precursor, e.g. by the product of the concentration and M.

Referring to FIG. 9, it can be seen that, by using the second order time derivative, characteristics (e.g. the stationary points) are more pronounced for line 74 (than what would be observed for the first order time derivative or line 72). The derivative 74 is processed to determine the peak to peak magnitude 84 for an adjacent maximum 80 and minimum 82, which is associated with initiation of the inhale. The initiation of inhale is determined as the maximum 80 as indicated by line 74.

The circuitry 8 may implement various conditions to search and locate the correct maximum 80 and minimum 82. These are exemplified for the implementation of the circuitry 8 shown in FIG. 7 as: determine possible maxima and minima for 1.5 seconds following initiation of the electrical energy to the heating system; determine greatest difference between adjacent maxima 80 and minima 82; disregard if time difference between adjacent maxima 80 and minima 82 is greater than 1 second; disregard if the absolute of peak to peak 84 is not greater than 0.19; the absolute of peak to peak 84 must be greater than that of an absolute of the peak to peak of a later occurring adjacent maximum and minimum multiplied by 1.18; the absolute of peak to peak 84 must be greater than that of an absolute of the peak to peak of an earlier occurring adjacent maximum and minimum multiplied by 1.13.

The circuitry 8 may determine the time duration $T_d$ of the electrical energy being applied to the heating system 30 by the previously described duration of actuation of the trigger (e.g. the vaping button or other suitable trigger). The circuitry 8 may determine the initiation of inhalation $T_i$ by the time of the maxima 80. A representative time duration of inhalation (which is not used in equation 1) may be determined by $T_d - T_i$.

Referring to FIGS. 10 and 11, which exemplify the current 72 and second order time derivative 78 for instances where the inhalation is initiated when the current has achieved the nominal value and is converging to the nominal value respectively, it can be seen that the peak to peak 84 may exhibit a similar magnitude in both instances. It may therefore be advantageous to utilise the second order derivative (as opposed to the first order derivative, or current without numerical differentiation) for determination of input values. Any dependency of the peak to peak magnitude 84 and the initiation time $T_i$ (due to exponential decay of the current) may be accounted for based on the dependence of Equation (1) on the initiation time $T_i$. Moreover, it is apparent that the second order derivative converges faster to a nominal value than current without numerical differentiation.

In a variant of Equation (1), if the inhalation is initiated sufficiently early, a saddle point in the current 72 may occur at line 74; consequently, the relationship may be adapted to search for a saddle point and to utilise the initiation of the point of zero gradient in the saddle (instead of the maxima at 80) to derive the peak to peak 84.

[Example 2]

An exemplary embodiment that implements one or more features of the previously described embodiments, or other embodiment disclosed herein, will now be provided.

The relationship provided in equation (2) may be implemented by circuitry 8 to determine the property of the flow, $$M = X \cdot T_d + Y \cdot V - Z \quad (2)$$

wherein the output value is the mass M (in mg) of aerosol present in a user inhale through the flow path 18. Coefficients X-Z are determined by regression of empirical data and have the respective values: −0.00003115; 0.1227; 295.2. The input values comprise: the constant voltage maintained over the heating system 30, denoted as "V" (in mV); the duration of the electrical energy applied to the heating system "$T_d$" (in mSec).

The above relationship will now be utilised by way of example:

The input values include: a voltage V of 2.51 V; a duration of the electrical energy $T_d$ of 3.987 seconds. The above relationship determines M as 12.7 mg with an experimental error of ±4-6%. The experimentally obtained value of M was obtained by measuring the depletion of a storage portion containing the precursor. A user inhale through the flow path was replicated by a pump with a calibrated representative flow rate of 18.33 ml/s.

The duration of the electrical energy $T_d$ through the heating system 30 can be determined as discussed for Example 1.

In instances wherein initiation of inhale cannot be determined (e.g. the maxima 80 cannot be identified), thus precluding implementation of Equation (1), then Equation (2) may be implemented to determine the property of the flow.

[Variant Examples]

It is to be understood that Example 1 and Example 2 provide example relationships between the electrical energy through the heating system 30 and the property of the flow of the flow path 18. Other relationships may be implemented.

A variant of Example 1 may include, as input values, one or more of: the period between the maximum 80 and minimum 82, or other period related thereto; the area under the maximum 80 and/or minimum 82; a magnitude of the maximum or minimum 82 (as opposed to the peak to peak value 84); alternative maxima and or minima may be used, including those associated with the end of the inhale. Alternatively, a gradient/period of the period between the oscillations caused by initiation and termination of inhalation may be utilised. In other variants, the input values may be obtained from a first derivative of the property of the electrical energy through the heating system 30, or of the property of the electrical energy through the heating system 30 (i.e. without numerical differentiation).

In a further variant, a feature of an oscillation in a property of the electrical energy through the heating system may be used as an input value, including as the only input value; e.g. Equation (1) is adapted to have, as the only input value, the peak to peak 84, which may be based on empirical data, which thus replaces the time dependency in the equation.

In a further variant, the duration of the user inhale may be obtained from the second order time derivative and may be used as an input value instead of the initiation time of the inhalation and/or duration of the electrical energy applied to the heating system.

A variant of Example 2 may include, as an input value, the duration of the user inhale, which may be determined from the second derivative of the property of the electrical energy through the heating system 30, or the property of the electrical energy through the heating system 30 (i.e. without numerical differentiation).

In other variants an alternative property related to the flow may be determined; e.g. equations (1) or (2) may be alternatively formulated to determine: volume of aerosol; mass or volume of flow (i.e. the summation of the aerosol and air); velocity of the flow.

[Output of Property Related to Flow]

The determined property of the flow may be utilised in various manners, depending on what it is. It may be utilised as one or more of the following: display to a user on a user interface (e.g. on a peripheral device, such as a smartphone 48, or on the apparatus 2); stored on a memory associated with the system 36; used as a basis for control of the apparatus 2 (e.g. it is determined that the depletion of precursor is greater than a threshold and aerosol generation is reduced or otherwise controlled).

Figure 5:
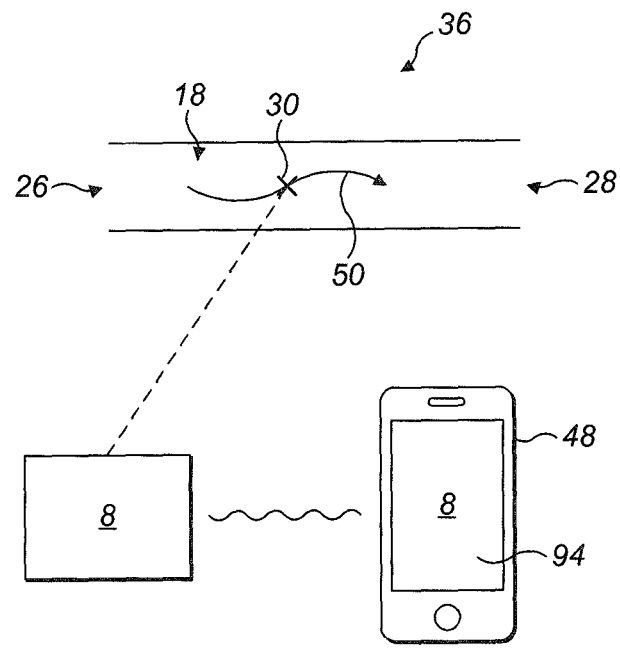
FIG. 5 is a schematic diagram showing embodiment componentry of the aerosol generation system of FIG. 1.

Referring to FIG. 5, in embodiments where the property of the flow is displayed on a user interface 94, the circuitry 8 generates instructions for the user interface 94 to display information based on the determined property of the flow. The instructions may be for processing, by a display driver, for driving the user interface 94. In embodiments wherein the property of the flow is an amount of one or more components of the aerosol present in an inhale, the quantity of said amount(s), and/or the amount from an aggregate of a plurality of inhales, may be displayed.

[Determination of Property Related to Flow Based on Initiation or Termination of User Inhale Through Flow Path]

Figure 13:
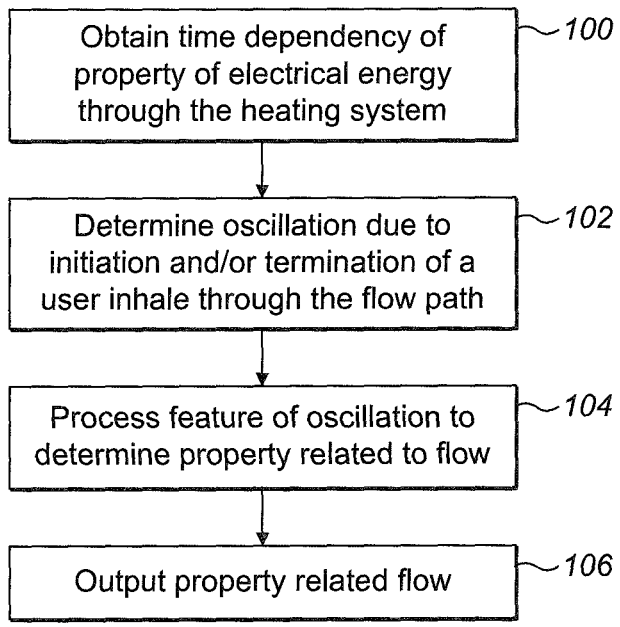
FIG. 13 is a flow diagram showing embodiment processes implemented by the system of FIG. 1 to determine a property of flow through said system, wherein the property is based on an oscillation in a property of the electrical energy through a heating system thereof, the oscillation being due to an initiation and/or termination of an inhalation of flow through said system.

Referring to FIG. 13, the described embodiments include circuitry 8 at block 100, to determine a property of electrical energy through the heating system 30; at block 102, the circuitry 8, to determine an oscillation due to initiation and/or termination of a user inhale through the flow path 18. The process may be implemented in combination with the embodiment process illustrated in FIGS. 4, and/or 12, or another embodiment disclosed herein.

As used herein "oscillation" may refer to one or more of: maxima; minima; saddle point. The maxima and minima may be adjacent. The oscillation may be caused by an inhalation through the flow path 18 (rather than by electrical noise or other interference). Furthermore, in embodiments, "oscillation" may refer to a certain feature or pattern of a parameter, such as (but not limited to) a feature or pattern of a property of electrical energy through the heating system. Referring to FIGS. 9 to 11, such a property may be, e.g., a current over time, and/or a first/second order derivative thereof. Hence, in such embodiments, an "oscillation" may occur at a portion of a function of a property, such as the functions illustrated by the graphs in FIGS. 9 to 11. For example, in FIG. 9 the portions of graphs 72 and/or 78 between line 74 and the vertical line (not shown) through point 82, or relatively close thereto, may be referred to as an "oscillation". Referring to FIGS. 10 and 11, an "oscillation" may be seen in the portions of graphs 72 and/or 78 between lines 74 and 81 or between 83 and 76.

As used herein, an "area of an oscillation" may refer to an area at least a section of whose boundary is formed by at least a section of the graph over time representing the oscillation. In an example, referring to FIG. 10, the area of the oscillation represented by the portion of graph 78 between lines 80 and 82 may thus refer to an area which is on one side bounded by the entire or part(s) of the portion of graph 78 between lines 80 and 82. Other sides of the area may be bounded by horizontal lines, such as the axis in the coordinate system which is denoted by "t" (the time axis) and/or by vertical lines, such as dashed lines 74 and 81 (or their extensions); or any other lines that are suited to define boundaries of an area.

As used herein, a "maximum" (of or comprised by an oscillation) may refer to a local maximum. Similarly, in embodiments, a "minimum" (of or comprised by an oscillation) may refer to a local minimum. In an example, referring to FIG. 10, the local maximum 80 and/or 108 of the oscillation as described above may be referred to as a "maximum". Similarly, the local minimum 82 and/or 110 of the oscillation as described above may be referred to as a "minimum". As can be seen in these examples, in preferred embodiments, an oscillation is bounded by a minimum and/or a maximum.

As used herein, an "amplitude" may refer to the absolute difference of a property of electrical energy through the heating system between different points of time. In an example, referring to FIG. 10, an "amplitude" may thus refer to the difference between a "maximum" and/or a "minimum" (peak to peak amplitude) as described above, such as illustrated by references 84 or 112. Alternatively, an "amplitude" may refer to the distance of a maximum or a minimum from the time axis (peak amplitude).

In embodiments, a "period of an oscillation" may refer to a duration of an "oscillation" as described above. Thus, in an example, a "period" may start and end at the endpoints of a respective "oscillation". However, the startpoint and endpoint of the oscillation may be freely chosen.

Referring to FIG. 13, at block 104, the circuitry 8 is configured to process one or more features of the oscillation to determine a property related to flow. The processing may include the one or more features used as the input values for the described relationship between the property of the electrical energy through the heating system 30 and the property of the flow of the flow path 18, with the property of the flow being the output value. At block 106, the circuitry 8 is configured to optionally output the property related to flow (as discussed previously).

Referring to the previously discussed Example 1, the property related to the flow of block 104 may include an amount of one or more components of aerosol dispensed in the inhale through the flow path 18. As discussed for Example 1, and with reference to FIGS. 10 and 11, an input value can be determined from the oscillation due to initiation of a user inhale through the flow path 18. The oscillation may be based on the second order time derivative 78, and includes a maximum 80 and an adjacent minimum 82. The peak to peak amplitude 84 can be extracted from the maximum 80 and minimum 82 and used as the input value.

In an embodiment, an input value can be determined from the oscillation due to termination of a user inhale through the flow path 18. The oscillation may be based on the second order time derivative 78, and includes a maximum 108 and an adjacent minimum 110. The peak to peak amplitude 112 can be extracted from the maxima 108 and minima 110 and used as the input value.

It has been found that the oscillation from either or both the initiation and termination of the inhale are related to an amount of one or more components of aerosol dispensed in the inhale through the flow path 18. In embodiments, input values may be determined from the oscillation due to termination and initiation. In embodiments, input values from one of the oscillation due to initiation or termination of the inhale may be used if the other is not available.

It will be understood that the implemented relationship between the electrical energy through the heating system 30 and the property of the flow of the flow path 18 can be selected, based on which input values are determined.

Referring to FIG. 9, after approximately 2.5 seconds, the current 72 exhibits notable oscillation (which can be more clearly seen in the corresponding second order time derivative 74). The oscillation is electrical noise caused by overheating of the heating element of the heating system 30. Depending on when the electrical noise occurs, the electrical noise may interfere with determination of the oscillation associated with the initiation and/or termination of inhalation. It may therefore be desirable to configure the circuitry 8 such that the user inhale through the flow path 18 occurs prior to the electrical noise, such that the electrical noise may not interfere with measurement of the inhale.

Referring to FIG. 9, the oscillation due to termination of inhale is interfered with by the electrical noise. It may therefore be difficult to accurately determine the oscillation due to termination of inhalation. Accordingly, it may be desirable to implement relationships (e.g. those discussed under Example 1) between the electrical energy through the heating system 30 and the property of the flow of the flow path 18 which do not require determination of the oscillation at termination of inhalation and require determination of oscillation at the initiation, since this oscillation is less likely to be subject to interference.

In variants, for determining the oscillation, the first derivative of the property of the electrical energy through the heating system 30 or the property of the electrical energy through the heating system 30 (i.e. without numerical differentiation) may be utilised.

However, with reference to FIG. 10 it can be seen that the second order derivative provides a more pronounced oscillation and may yield more accurate output values.

In embodiments, the circuitry 8 may determine the oscillation due to inhalation and/or termination of the inhalation by comparison to one or more predetermined conditions, which are exemplified under Example 1 in relation to conditions to search and locate the maxima and minima.

In variants embodiments, other features of the oscillation may be utilised as the input value, e.g. the period between the maxima and minima, or other periods related thereto; the area under the maxima and/or minima; a magnitude of the maxima or minima (as opposed to the peak to peak value).

Considering Example 1, it can be understood that the magnitude of the amplitude 84 is directly related to an amount of the one or more components M of aerosol dispensed, i.e. via the empirical relationship of Equation 1; the greater the magnitude of the amplitude the greater the amount of the component dispensed, e.g. via direct proportionality or other mathematical function relationship.

[Plurality of Relationships to Determine Property of Flow Implemented by Circuitry]

The described embodiments may be implemented with the electrical circuitry 8 to determine a property related to the flow of the flow path 18 based on one of a plurality of different relationships between the electrical energy through the heating system and said property.

In particular, the circuitry may implement a process comprising: measuring a property of the electrical energy through the heating system (e.g. the current as described previously or another property such as power or voltage); determining one or more characteristics from said measured property of the electrical energy (e.g. the input values for the previously described Example 1 or Example 2 or the herein described related variants or other like characteristics); selecting, based on the determined characteristics, one from a plurality of different empirical relationships between the measured property of the electrical energy and a property of the flow as defined herein (e.g. selecting Example 1 or Example 2 or another of the herein described related variants); implementing said relationship to determine the property of the flow as defined herein.

Suitable examples of relationships are provided as Example 1 and Example 2 and the herein described related variants. Accordingly, in an embodiment, the circuitry 8 may implement the relationship (e.g. Example 1 or Example 2 or other variant) according to an order of preference or a set of input values, which may be referred to as a "class".

Referring to FIG. 14, an embodiment process for implementing the plurality of relationships includes, at block 114, the circuitry 8 measuring the property of the electrical energy through the heating system 30 (examples of which were previously discussed).

At condition 116, the circuitry 8 determines whether a first class of one or more input values can be determined from the determined property of the electrical energy through the heating system 30. If the first class can be determined, then block 118 is executed to output the property of the flow at block 120. Block 118 implements a first relationship.

In an embodiment which implements Equation (1) of Example 1, the first class would be: the peak to peak magnitude 84, which is denoted as "I"; the constant voltage maintained over the heating system 30, which is denoted as "V"; the duration of the electrical energy applied to the heating system "$T_d$"; the initiation time of the inhalation "$T_i$". Hence at condition 116, if the first class can be determined, then at block 118 Equation (1) is implemented. At block 120 the output value is the mass M of aerosol present in a user inhale through the flow path 18.

If at condition 116 the first class cannot be determined (e.g. one or more of the input values cannot be computed), then condition 122 is executed. At condition 112 the circuitry 8 determines whether a second class of one or more input values can be determined from the determined property of the electrical energy through the heating system 30. If the second class can be determined, then block 124 is executed to output the property of the flow at block 120. Block 124 implements a second relationship.

In an embodiment which implements Equation (2) of Example 2, the second class would be: the duration of the electrical energy applied to the heating system "$T_d$". Hence, at condition 116, if the second class can be determined, then at block 124 Equation (2) is implemented. At block 120 the output value is the mass M of aerosol present in a user inhale through the flow path 18.

In variant embodiments, a greater number than two relationships are implemented. In embodiments, the classes associated with a plurality of relationships may be determined, with the particular relationship implemented according to an order of preference.

If at condition 116 the second class cannot be determined (e.g. one or more of the input values cannot be computed), then block 126 is executed. At block 126 the circuitry 8 may determine the output value based on an output value determined from one or more prior user inhales through the flow path 18 (e.g. the output value from the previous inhalation is utilised as the output value or an average or other suitable representation based on output values from a plurality of prior inhalations is utilised as the output value). The information relating to prior output values may be stored on a memory communicatively coupled to a processor of the circuitry 8.

Referring to the preceding embodiment in which Equation (1) and (2) were implemented as the first and second relationships, the input values of the second class associated with the second relationship is a subset of the input values of the first class associated with the first relationship. Electrical circuitry 8 implemented in this manner allows the second relationship to be conveniently implemented using one or more of the input values of the first class in the event that all of those from the first class cannot be determined. Such an implementation may have reduced processing overhead.

Embodiments are also provided according to the following clauses:

Clause 1. An aerosol generation system (36) for generation of an aerosol from an aerosol-forming precursor, the system comprising: an electrically operated heating system (30) to heat said precursor to generate the aerosol; a flow path (18) for transmission of flow, including the aerosol, to a user; the heating system arranged in fluid communication with the flow path; electrical circuitry (8) to determine a characteristic associated with a second order time derivative of a property of electrical energy through the heating system, and to determine a property related to the flow of the flow path based on the characteristic of the second order time derivative.

Clause 2. The system of clause 1 or another embodiment disclosed herein, wherein the property of the electrical energy is based on one or more of: electrical current through the heating system (30); electrical power through the heating system; electrical potential over the heating system.

Clause 3. The system of any preceding clause or another embodiment disclosed herein, wherein the property related to the flow is one or more of: an amount of one or more components of the aerosol or flow, which may be measured by mass or volume; a start of an inhale; an end of an inhale; a duration of an inhale.

Clause 4. The system of any preceding clause or another embodiment disclosed herein, wherein the characteristic of a second order time derivative is based on a property of an oscillation (80, 82) in the second order time derivative.

Clause 5. The system of any clause 4 or another embodiment disclosed herein, wherein the oscillation comprises a maxima and adjacent minima associated with initiation and/or termination of a user inhale through the flow path. Adjacent may refer to immediately proximate, which may include without a period of baseline adjoining the maxima and minima.

Clause 6. The system of any clause 5 or another embodiment disclosed herein, wherein the characteristic is a peak to peak amplitude (84) of the maxima and adjacent minima.

Clause 7. The system of any preceding clause or another embodiment disclosed herein, wherein the electrical circuitry (8) to apply electrical energy to preheat the heating system (30) prior to a user inhale through the flow path (18).

Clause 8. The system of any preceding clause or another embodiment disclosed herein, wherein the circuitry (8) to determine the property of the electrical energy through the heating system (30) during a user inhale through the path.

Clause 9. The system of any preceding clause or another embodiment disclosed herein, wherein the electrical circuitry (8) to generate instructions for a user interface to display information based on the determined property of the flow.

Clause 10. The system of any preceding clause or another embodiment disclosed herein, wherein the electrical circuitry (8) to determine the property related to the flow based on a stored relationship between the property related to the flow and the characteristic associated with a second order time derivative. The relationship may include an empirical relationship.

Clause 11. The system of any preceding clause or another embodiment disclosed herein, wherein the electrical circuitry (8) includes one or more electronic processors communicatively coupled to a memory.

Clause 12. The system of any preceding clause or another embodiment disclosed herein, wherein the system (36) includes housing (35) arranged to house at least part of the flow path (18), the heating system (30) and a precursor transmission unit (16) for transmission of precursor to the heating system (30) from a storage (14).

Clause 13. A method of determining a property of a flow of an aerosol generation system (36). The method may include the system of any preceding clause or another embodiment disclosed herein. The method comprising: determining a characteristic associated with a second order time derivative of a property of electrical energy through a heating system; determining the property related to the flow based on the characteristic of the second order time derivative.

Clause 14. An aerosol generation system (36) for generation of an aerosol from an aerosol-forming precursor. The system may include the system any preceding clause or another embodiment disclosed herein. The system comprising: an electrically operated heating system (30) to heat said precursor to generate the aerosol; a flow path (18) for transmission of flow, including the aerosol, to a user; the heating system arranged in fluid communication with the flow path; electrical circuitry (8) to apply at least a predetermined amount of electrical energy to the heating system to stabilise a property of electrical energy through the heating system, the electrical circuitry to determine a property related to the flow of the flow path based on the stabilised property of the electrical energy through the heating system. The stabilised property may be subsequent to the applied predetermined amount of electrical energy.

Clause 15. The system of clause 14 or any preceding clause or another embodiment disclosed herein, wherein the electrical circuitry is operable to apply the predetermined amount of electrical energy over a first time period, and to determine the property related to the flow over a subsequent second time period.

Clause 16. The system of any preceding clause or another embodiment disclosed herein, wherein the first time period is between 0.3 and 2 or 0.6-1.5 seconds.

Clause 17. The system of any preceding clause or another embodiment disclosed herein, wherein the predetermined amount of electrical energy is at least 10-50 or 15-40 Joules ±40% or ±20%.

Clause 18. The system of any preceding clause or another embodiment disclosed herein, wherein the electrical circuitry (8) to determine user actuation of a trigger an in response to apply said predetermined amount of electrical energy through the heating system (30). The trigger may be a manually actuated actuator, which may be for actuation by a digit of a hand of a user, e.g. a button.

Clause 19. The system of any preceding clause or another embodiment disclosed herein, wherein the predetermined amount of electrical energy is to preheat the heating system (30) to a predetermined temperature range. The temperature may be reduced by thermal energy transfer into the flow during a user inhale through the flow path. The predetermined temperature range may be 150-350° C.

Clause 20. The system of any preceding clause or another embodiment disclosed herein, wherein the property of electrical energy through the heating stabilised by the predetermined amount of electrical energy is the electrical current or electrical potential or electrical power.

Clause 21. The system of any preceding clause or another embodiment disclosed herein, wherein the predetermined amount of electrical energy is to stabilise the property of the electrical energy through the heating system (30) to ±25% or ±40% of a nominal value.

Clause 22. The system of any preceding clause or another embodiment disclosed herein, wherein the electrical circuitry is to determine the property of the flow is during a user inhale through the flow path.

Clause 23. The system of any preceding clause or another embodiment disclosed herein, the electrical circuitry (8) to determine the property related to the flow based on a relationship between the property related to the flow and the characteristic associated with a second order time derivative of the property of the electrical energy through the heating system (30).

Clause 24. The system of any preceding clause or another embodiment disclosed herein, wherein the property related to the flow is one or more of: an amount of one or more components of the aerosol; a start of an inhale; an end of an inhale; a duration of an inhale.

Clause 25. The system of any preceding clause or another embodiment disclosed herein, wherein the electrical circuitry (8) is to maintain constant a property of the electrical energy to the heating system, wherein said constant property is different to the property of the electrical energy through the heating system to the determine the property related to the flow of the flow path. The constant property may be one of the current, electrical potential, power.

Clause 26. A method of determining a property of a flow of an aerosol generation system (36). The method may include the system or method of any preceding clause or another embodiment disclosed herein. The method comprising: applying a predetermined amount of electrical energy to a heating system (30) to stabilise a property of electrical energy through the heating system; determining the property related to the flow based on the stabilised property of the electrical energy through the heating system.

Clause 27. An aerosol generation system (36) for generation of an aerosol from an aerosol-forming precursor. The system may include the system any preceding clause or another embodiment disclosed herein. The system comprising: an electrically operated heating system (30) to heat said precursor to generate the aerosol; a flow path (18) for transmission of flow, including the aerosol, to a user; the heating system arranged in fluid communication with the flow path; electrical circuitry (8) to determine a property related to the flow of the flow path based on one of a plurality of different relationships between the electrical energy through the heating system and said property. The relationship may include a property of the electrical energy through the heating system, e.g. current, power or and electrical potential.

Clause 28. The system of any preceding clause or another embodiment disclosed herein, wherein the electrical circuitry to implement one of the plurality of said relationships according to an order of preference.

Clause 29. The system of any preceding clause or another embodiment disclosed herein, wherein a first relationship comprises an output value of the property of the flow related to first one or more input values determined based on the electrical energy through the heating system.

Clause 30. The system of any preceding clause or another embodiment disclosed herein, wherein the electrical circuitry (8) to determine if said first one or more input values can be obtained based on the electrical energy through the heating system, and if obtainable to determine the output value based on the first relationship. The circuitry may determine if said values can be obtained in respect of a user inhale through the flow path.

Clause 31. The system of any preceding clause or another embodiment disclosed herein, wherein the first one or more input values is based on one or more of an: amplitude of an oscillation in the second order time derivative of said electrical energy, e.g. an oscillation due to initiation and/or termination of an inhalation; an initiation time of a user inhale through the flow path; a duration of a user inhale through the flow path; a duration of electrical energy applied to the heating system.

Clause 32. The system of any preceding clause or another embodiment disclosed herein, wherein the electrical circuitry (8) to determine if said first one or more input values are unobtainable based on the electrical energy through the heating system, and to determine the output value based on another of the plurality of said relationships or the information according to clause 37.

Clause 33. The system of any preceding clause or another embodiment disclosed herein, wherein a second relationship comprises the output value related to second one or more input values determined based on the electrical energy through the heating system, the electrical circuitry (8) to determine if said second one or more input values can be obtained based on the electrical energy through the heating system, and if obtainable to determine the output value based on the second relationship.

Clause 34. The system of any preceding clause or another embodiment disclosed herein, wherein the second one or more input values are a subset of one or more of the first input values.

Clause 35. The system of any preceding clause or another embodiment disclosed herein, wherein the second one or more input values is based on a duration of a user inhale through the flow path or a duration of electrical energy applied to the heating system.

Clause 36. The system of any preceding clause or another embodiment disclosed herein, wherein the electrical circuitry (8) to determine if said second one or more input values from are unobtainable based on the electrical energy through the heating system, and to determine the output value based on another of the plurality of said relationships or based on information related to one or more prior user inhales through the flow path.

Clause 37. The system of clause 36 or another embodiment disclosed herein, wherein said information is based on an output value determined from a prior user inhale. The information may be based on an output value determined from one or more a prior user inhales, e.g. an average, or other representative quantity of a plurality of inhales. The information may be based on a stored amount, e.g. a default value.

Clause 38. The system of any preceding clause or another embodiment disclosed herein, wherein the output value is an amount of one or more components of aerosol dispensed during a user inhalation through the flow path.

Clause 39. An aerosol generation system (36) for generation of an aerosol from an aerosol-forming precursor. The system may include the system any preceding clause or another embodiment disclosed herein. The system comprising: an electrically operated heating system (30) to heat said precursor to generate the aerosol; a flow path (18) for transmission of flow, including the aerosol, to a user; the heating system arranged in fluid communication with the flow path; electrical circuitry (8) to determine one of a plurality of classes, the classes comprising one or more input values based on the electrical energy through the heating system and to determine an output value related to a property related to the flow of the flow path based on one of a plurality of different relationships between the electrical energy through the heating system and said property, wherein the relationship is selected according to the determined class.

Clause 40. A method of determining a property of a flow of an aerosol generation system (36). The method may include the system or method of any preceding clause or another embodiment disclosed herein. The method comprising: determining the output value based on one of a plurality of different relationships between the electrical energy through the heating system and said output value.

Clause 41. An aerosol generation system (36) for generation of an aerosol from an aerosol-forming precursor. The system may include the system any preceding clause or another embodiment disclosed herein. The system comprising: an electrically operated heating system (30) to heat said precursor to generate the aerosol; a flow path (18) for transmission of flow, including the aerosol, to a user; the heating system arranged in fluid communication with the flow path; electrical circuitry (8) to determine a feature of an oscillation of a property of electrical energy through the heating system, the oscillation due to initiation and/or termination of a user inhale through the flow path, and to determine an amount of one or more components of aerosol dispensed in the inhale based on the feature of the oscillation. Said feature may refer to one or more features of said oscillation. The amount of said one or more component may be the total dispensed for the inhale.

Clause 42. The system of any preceding clause or another embodiment disclosed herein, wherein the oscillation comprises a maxima and/or minima, which may be adjacent.

Clause 43. The system of any preceding clause or another embodiment disclosed herein, wherein the feature of the maxima and/or minima includes one or more of: an amplitude (including the peak to peak of the maxima and minima); a period; an area bounded by the maxima and/or minima. The amplitude may be a peak to peak amplitude of adjacent maxima and minima.

Clause 44. The system of any preceding clause or another embodiment disclosed herein, wherein the oscillation is determined from a second order time derivative of the property of electrical energy through the heating system.

Clause 44. The system of any preceding clause or another embodiment disclosed herein, wherein the electrical circuitry (8) is to determine the property of the flow during a user inhale through the flow path.

Clause 45. The system of any preceding clause or another embodiment disclosed herein, wherein the electrical circuitry (8) to determine the oscillation due to initiation and/or termination of a user inhale through the flow path by comparison to one or more predetermined conditions. The circuitry may implement various conditions to search for the maxima and/or minima, including comparison of one or more of: period; amplitude; position in time with respect to other maxima and/or minima.

Clause 46. An aerosol generation system (36) for generation of an aerosol from an aerosol-forming precursor. The system may include the system any preceding clause or another embodiment disclosed herein.

Clause 47. A method of determining a property of a flow of an aerosol generation system (36). The method may include the system or method of any preceding clause or another embodiment disclosed herein. The method comprising: determining a feature of an oscillation of a property of electrical energy through a heating system, the oscillation due to initiation and/or termination of a user inhale through the flow path, determining an amount of aerosol dispensed in the inhale based on the feature of the oscillation.

Clause 48. A computer program when run on programmable electric circuity (6), to execute the method of clause 13 or 26 or 40 or 47, or any preceding clause or another embodiment disclosed herein.

Clause 49. Electric circuitry (8) for an electrically operated aerosol generation system, said circuitry to implement the method of clause 13 or 26 or 40 or 47 or any preceding clause or another embodiment disclosed herein.

Clause 50. A computer readable medium comprising the computer program of clause 48.

It will be appreciated that any of the disclosed methods (or corresponding apparatuses, programs, data carriers, etc.) may be carried out by either a host or client, depending on the specific implementation (i.e. the disclosed methods/apparatuses are a form of communication(s), and as such, may be carried out from either 'point of view', i.e. in corresponding to each other fashion). Furthermore, it will be understood that the terms "receiving" and "transmitting" encompass "inputting" and "outputting" and are not limited to an RF context of transmitting and receiving radio waves. Therefore, for example, a chip or other device or component for realizing embodiments could generate data for output to another chip, device or component, or have as an input data from another chip, device or component, and such an output or input could be referred to as "transmit" and "receive" including gerund forms, that is, "transmitting" and "receiving", as well as such "transmitting" and "receiving" within an RF context.

As used in this specification, any formulation used of the style "at least one of A, B or C", and the formulation "at least one of A, B and C" use a disjunctive "or" and a disjunctive "and" such that those formulations comprise any and all joint and several permutations of A, B, C, that is, A alone, B alone, C alone, A and B in any order, A and C in any order, B and C in any order and A, B, C in any order. There may be more or less than three features used in such formulations.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

Unless otherwise explicitly stated as incompatible, or the physics or otherwise of the embodiments, example or claims prevent such a combination, the features of the foregoing embodiments and examples, and of the following claims may be integrated together in any suitable arrangement, especially ones where there is a beneficial effect in doing so. This is not limited to only any specified benefit, and instead may arise from an "ex post facto" benefit. This is to say that the combination of features is not limited by the described forms, particularly the form (e.g. numbering) of the example (s), embodiment(s), or dependency of the claim(s). Moreover, this also applies to the phrase "in one embodiment", "according to an embodiment" and the like, which are merely a stylistic form of wording and are not to be construed as limiting the following features to a separate embodiment to all other instances of the same or similar wording. This is to say, a reference to 'an', 'one' or 'some' embodiment(s) may be a reference to any one or more, and/or all embodiments, or combination(s) thereof, disclosed. Also, similarly, the reference to "the" embodiment may not be limited to the immediately preceding embodiment.

As used herein, any machine executable instructions, or compute readable media, may carry out a disclosed method, and may therefore be used synonymously with the term method, or each other.

The foregoing description of one or more implementations provides illustration and description, but is not intended to be exhaustive or to limit the scope of the invention to the precise form disclosed. Modifications and variations are possible in light of the above teachings or may be acquired from practice of various implementations of the present disclosure.

LIST OF REFERENCES

36 System
2 Apparatus
4 Power supply
6 Atomizer
20 Precursor inlet
22 Flow inlet
24 Outlet
30 Heating system
8 Circuitry
52 Measurement system
58 Shunt resistor
60 Amplifier
62 Filter
54, 64 Processor
56 DC:DC converter
10 Precursor transmission system
14 Storage portion
16 Transmission unit
12 Delivery system
34 Mouthpiece
18 Flow path
26 Inlet
28 Outlet
50 flow
32 Cartomizer
36 Housing
34 Mouthpiece
42 Peripheral device
94 User interface

The invention claimed is:

1. An aerosol generation system for generation of an aerosol from an aerosol-forming precursor, the system comprising:
   an electrically operated heating system to heat said precursor to generate the aerosol;
   a flow path for transmission of flow, including the aerosol, to a user, the heating system arranged in fluid communication with the flow path; and
   electrical circuitry including one or more electronic processors configured
      to determine a characteristic associated with a second order time derivative of a property of electrical energy through the heating system, and
      to determine a property related to the flow of the flow path based on the characteristic of the second order time derivative.

2. The system of claim 1, wherein the property of the electrical energy is based on an electrical current through the heating system.

3. The system of claim 1, wherein the property related to the flow is one or more of: an amount of one or more components of the aerosol, a start of an inhale, an end of an inhale, and a duration of an inhale.

4. The system of claim 1, wherein the characteristic associated with the second order time derivative is based on a property of an oscillation in the second order time derivative.

5. The system of claim 4, wherein the property of the oscillation comprises one of: an amplitude, an area, and a period, of the oscillation.

6. The system of claim 4, wherein the oscillation comprises and/or is bounded by a maximum and adjacent minimum associated with initiation and/or a maximum and adjacent minimum associated with termination of a user inhale through the flow path.

7. The system of claim 6, wherein the characteristic is a peak to peak amplitude of the maxima and adjacent minima.

8. The system of claim 1, wherein the electrical circuitry is configured to apply electrical energy to preheat the heating system prior to a user inhale through the flow path.

9. The system of claim 1, wherein the one or more electronic processors are configured to generate instructions for a user interface to display information based on the determined property of the flow.

10. The system of claim 1, wherein the one or more electronic processors are configured to determine the property related to the flow based on a stored relationship between the property related to the flow and the characteristic associated with the second order time derivative.

11. The system of claim 1, wherein the one or more electronic processors are communicatively coupled to a memory.

12. The system of claim 1, wherein the system includes a housing arranged to house at least part of the flow path, the heating system and a precursor transmission unit for transmission of precursor to the heating system from a storage.

13. A method of determining a property of a flow of an aerosol generation system for generation of an aerosol from an aerosol-forming precursor, the aerosol generation system comprising an electrically operated heating system to heat said precursor to generate the aerosol, and a flow path for transmission of flow, including the aerosol, to a user, wherein the heating system is arranged in fluid communication with the flow path, the method comprising:
   determining a characteristic associated with a second order time derivative of a property of electrical energy through the heating system; and
   determining the property related to the flow based on the characteristic of the second order time derivative.

14. A non-transitory computer readable medium comprising instructions which, when executed, executes the method of claim 13.

15. Electric circuitry for an electrically operated aerosol generation system, said circuitry configured to implement the method of claim 13.

\* \* \* \* \*